United States Patent [19]
Schold et al.

[11] Patent Number: 6,017,962
[45] Date of Patent: Jan. 25, 2000

[54] METHOD OF DEPLETION OF METHIONINE IN PLASMA AND SOLID TUMORS AND USES THEREOF

[75] Inventors: Clifford S. Schold; Demetrius M. Kokkinakis, both of Dallas, Tex.

[73] Assignee: Board of Regents, The University of Texas System, Austin, Tex.

[21] Appl. No.: 08/807,193

[22] Filed: Feb. 27, 1997

[51] Int. Cl.[7] .......................... A61K 31/195; A61K 38/51; A61K 38/52; A61K 38/53

[52] U.S. Cl. .......................... 514/562; 424/94.5

[58] Field of Search ............................. 514/562; 424/94.5

[56] References Cited

PUBLICATIONS

Kreis, Willis; Hession, Catherine; *Biological Effects of Enzylmatic Deprivation of L–Methioine in Cell Culture and an Experimental Tumor.* Cancer Research 33, 1866–1869, (Aug. 1973).

Lishko, Valeryi K.; Lishko, Olga V.; Hoffman, Rovert M.; *Depletion of Serum Methionine by Methioninase in Mice.* AntiCancer Research 13, 14655–1468 (1993).

Breillout, T.;' Hadida, F.; Echinard–Garin, P.; Lascaux, V.; Poupon, M.–F.; *Decreased Rat Rhabdomyosarcoma Pulmonary Metastases in Response to a Low Methionine Diet.* AntiCancer Research 7, 861–868 (1987).

Narihide Goseki, MD.; Sigeru Yalmazaki, MD.; Mitsuo Endo, MD.; Tokio Onodera, MD.; Goro Kosaki, MD.; Yutaka Hibino, Mse; Tokuo Kuwahata, BSPharm; *Antitumor Effect of Methionine–Depleting Total Parenteral Nutrition With Doxorubicin Administration on Yoshida Sarcoma–Bearing Rats.* Cancer &, 1865–1872 (Apr. 1, 1992).

Lishko, Valeryi K.; Lishko, Olga V.; Hoffman, Rovert M.; *Depletion of Serum Methionine by Methioninase in Mice.* AntiCancer Research 13, 14655–1468 (1993).

*Primary Examiner*—Jerome D. Goldberg
*Attorney, Agent, or Firm*—Arnold, White & Durkee

[57] ABSTRACT

The present invention provides a method of depleting methionine in the plasma of an individual in need of such treatment, comprising the steps of: administering to said individual a pharmacologically effective amount of a methionine scavenger; and treating said individual with homocystine. Also provided is a method of method of treating a methionine-dependent tumor in an individual in need of such treatment, comprising the steps of: administering to said individual a pharmacologically effective amount of a methionine synthetase inhibitor; treating said individual with homocystine while depriving dietary methionine, homocysteine and choline; and administering to said individual a pharmacologically effective amount of an anti-neoplastic alkylating agent.

8 Claims, 11 Drawing Sheets

METHOD OF DEPLETION OF METHIONINE IN PLASMA AND SOLID TUMORS AND USES THEREOF

BACKGROUND OF THE INVENTION

1. Field of the Invention

The present invention relates generally to the fields of oncology and the pharmacotherapy of neoplastic disease. More specifically, the present invention relates to a method of depletion of methionine in plasma and solid tumors and uses thereof.

2. Description of the Related Art

Methionine (MET)[4] is essential for normal growth and development of mammals. This amino acid participates in: (1) protein synthesis (Tautt, et al., 1982); (2) numerous S-adenosylmethionine dependent transmethylation reactions (Stern et al., 1984); (3) the formation of polyamines spermidine and spermine (Pegg et al., 1984); (4) synthesis of cystathionine, cysteine and other metabolites of the transulfuration pathway; (5) the supply of homocysteine (HCY)[4], which is needed for metabolism of intracellular folates; and (6) the catabolism of choline (Finkelstein, 1990).

With very few exceptions, normal cells can use homocysteine in place of methionine to support all of the above reactions (Hoffman, 1990; Guo, et al., 1993). In contrast to normal cells, a large number of cultured tumor cells and about 25% of fresh human tumors grown in histocultures cannot effectively utilize homocysteine in place of methionine, and such cells or tumors are classified as methionine-dependent (Guo, et al., 1993a; Guo, et al., 1993b). There is substantial evidence that methionine dependence occurs more frequently in metastatic tumor cells (Breillout, et al., 1987; Breillout, et al., 1990; Liteplo, 1990.), although reversion of dependence is not necessarily linked to loss of metastatic potential (Vanhamme, 1989). The biochemical basis for methionine dependency is not yet fully understood. Methionine-dependent tumor cells appear to synthesize methionine from homocysteine by an active methionine synthase, but at levels not adequate to both sustain growth and meet their high transmethylation requirements (Judde, et al., 1989). The most likely biochemical defect leading to methionine dependency is thought to be related to the synthesis and availability of methylcobalamine, which is directly involved in the transfer of methyl groups from 5-methyltetrahydrofolate to homocysteine (Liteplo, et al., 1991; Fiskerstrand, et al., 1994).

The defect in homocysteine utilization has been extensively investigated in order to induce selective killing of tumors while sparing normal tissues. Lack of methionine results in a reversible blockage of rapidly proliferating tumor cells in the late S and G2 phases of the cell cycle (Stern, et al., 1986; Guo, et al., 1993a). In general, cells arrested in S, G2 or M are not only susceptible to spontaneous death, as compared to cells arrested in G1, but they are also supersensitive to various chemotherapeutic drugs, such as doxorubicin, which blocks and kills in G2 (Stern, et al., 1986). Methionine-depleting diets in combination with chemotherapy suppress metastasis of Yoshida sarcoma and rhabdomyosarcoma tumors in animals (Breillout, et al., 1987; Goseki, et al., 1992). Potentiation of many drugs, some of which act by damaging cellular DNA, indicates that methionine deprivation may compromise DNA repair ability in addition to causing premitotic cell cycle blocks and cell death in tumors.

Modulation of resistance of tumor cells to chemotherapy may encompass a large number of mechanisms including those involved in the processing of the agent (metabolism, conjugation, etc), its transport into or its elimination from the target cell, or the reversal or repair of the damage induced by such agents. One or more of these mechanisms may be compromised in tumors by methionine deprivation, thus selectively sensitizing tumor cells to chemotherapy. A systematic study of the modulation of such mechanisms by deprivation of methionine will allow the deployment of the full potential of methionine dependence phenotype in the treatment of several tumors.

The prior art is deficient in the lack of effective means of depleting the levels of methionine in plasma and treatment of methionine-dependent tumors. The present invention fulfills this longstanding need and desire in the art.

SUMMARY OF THE INVENTION

Methionine (MET)-dependent tumor cell lines require methionine to proliferate and homocysteine (HCY) does not substitute for this requirement. In that context, the effect of methionine withdrawal on the ability of tumor cells to repair $O^6$-alkylguanine adducts by $O^6$-methylguanine-DNA methyltransferase (MGMT) was examined. Such adducts are major contributors to the toxicity of alkylating antitumor agents, such as procarbazine, temozolomide, carmustine and related nitrosoureas commonly used for the treatment of several tumors. From six $O^6$-methylguanine-DNA methyltransferase (MGMT) efficient (mer$^+$) cell lines tested, two medulloblastomas (Daoy and D-341) and a lung non-small cell adenocarcinoma with metastatic potential (H-1623) were most sensitive to methionine deprivation while two glioblastomas (U-138, D-263) and a small cell lung carcinoma H-1944 were moderately to weakly dependent. Regardless of the degree of methionine dependence, all of these lines downregulated their MGMT activity within 48 to 72 hrs of transfer from MET$^+$HCY$^-$ to MET$^-$HCY$^+$ media, long before the eradication of the culture. Reduction of MGMT activity was due to a decline of both MGMT mRNA and protein levels. Methionine -dependent, mer$^+$ tumor cells cultured in MET$^-$HCY$^+$ were more sensitive to the chemotherapeutic agent carmustineBCNU ($IC_{50}$=5–10 $\mu$M) than those cultured in MET$^+$HCY$^-$ ($IC_{50}$=45–90 $\mu$M), while MET-independent or mer$^-$ tumor cell lines and normal cells were unaffected. This indicates that reduction of MGMT imposed by the absence of methionine, renders mer$^+$ tumor cells more susceptible to alkylating agents. The relatively selective suppression of MGMT activity in mer$^+$, MET$^-$ dependent tumor cells in combination with the inability of such cells to proliferate in the absence of methionine, may lead to the development of more effective treatment strategies for mer$^+$, methionine-dependent tumors. Since more than 80% of human tumors are mer$^+$ and more than 50% of them are moderately to strongly dependent on MET, the method is expected to have wide application in cancer treatment.

In one embodiment of the present invention, there is provided a method of depleting methionine in the plasma of an individual in need of such treatment, comprising the steps of: restricting intake of methionine, homocysteine and choline in the diet of said individual; administering to said individual a pharmacologically effective amount of a methionine scavenger; and treating said individual with homocystine.

In another embodiment of the present invention, there is provided a method of treating a methionine-dependent tumor in an individual in need of such treatment, comprising the steps of: restricting intake of methionine, homocysteine and choline in the diet of said individual; administering to said individual a pharmacologically effective amount of a methionine scavenger; treating said individual with homocystine; and administering to said individual a pharmacologically effective amount of an anti-neoplastic alkylating agent.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 7 shows an amino acid analysis in plasma of nude mice fed a met$^-$hcy$^-$chl$^-$ (A) or met$^-$hcy$^+$chl$^-$ (B) diets for 24 hours hand then injected with a methionine precursor (50 mg/kg) and methioninase (1000 u/kg) both administered ip and 2 hours apart.

DETAILED DESCRIPTION OF THE INVENTION

Figure 1:
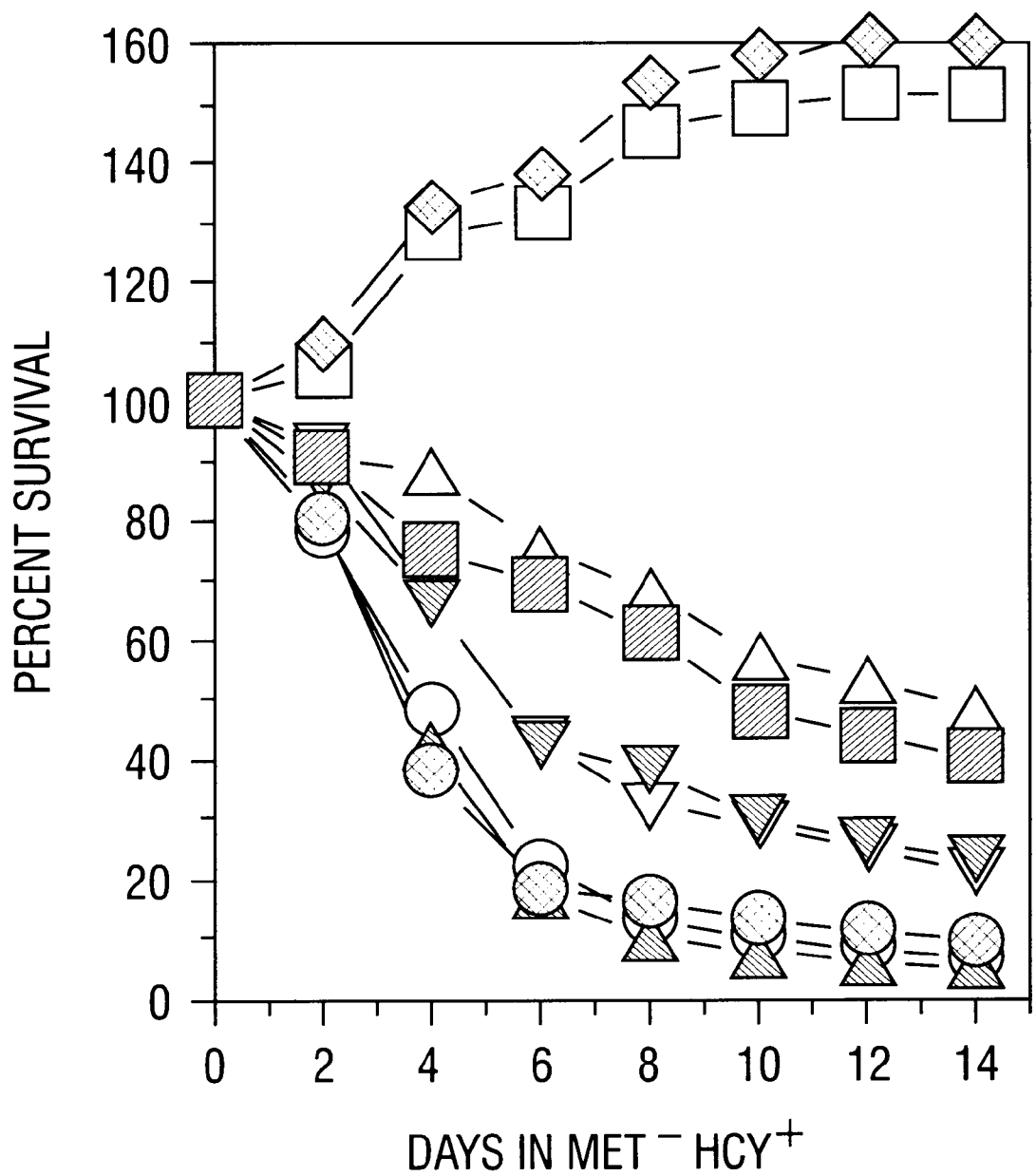
FIG. 1 shows the effect of replacement of methionine with homocysteine on cultures of the Daoy (o), D-341 (•), U-138 (∇), D-263 (filled upside down triangle), H-1944 (Δ), H-1623 (filled triangle), U-87 (unfilled square), SWB-40 (filled square) and NIH-3T3 (♦). Cells growing exponentially in MET$^+$HCY$^-$ were washed with PBS two times and seeded in MET$^-$HCY$^+$ medium. Cultures were trypsinized and live cells, as determined by trypan blue exclusion, were counted.
Figure 2A:
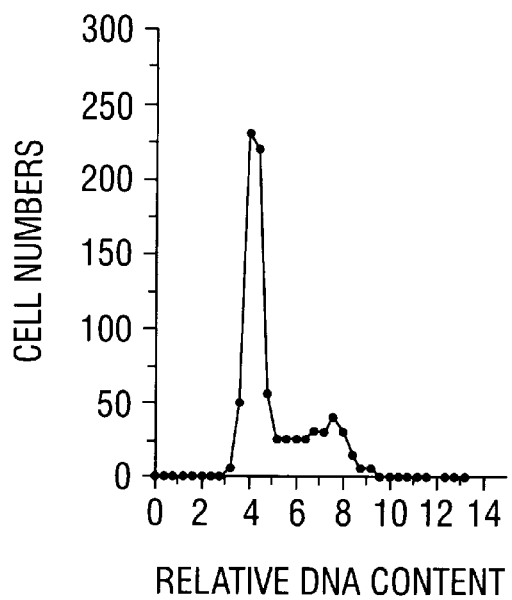
FIG. 2 shows the effect of replacement of methionine with homocysteine on the distribution of cell populations of Daoy in G1, S and G2 compartments. Cell cycle distribution in MET$^+$HCY$^-$ (FIG. 2A) and MET$^-$HCY$^+$ after 2 days (FIG. 2B), 4 days (FIG. 2C), and 6 days (FIG. 2D) days of culture. A G$_2$ block results in a shift of distribution from G1 to G2 as early as day 2.
Figure 2B:
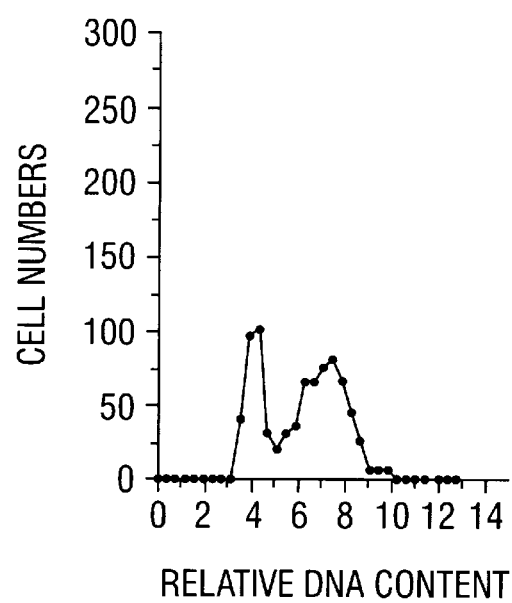
Figure 2C:
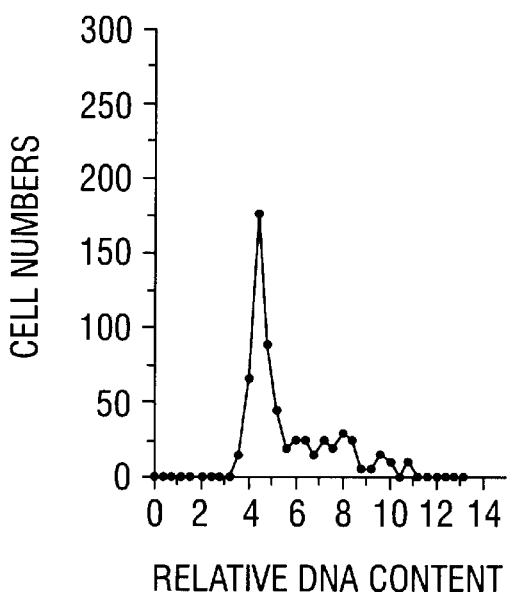
Figure 2D:
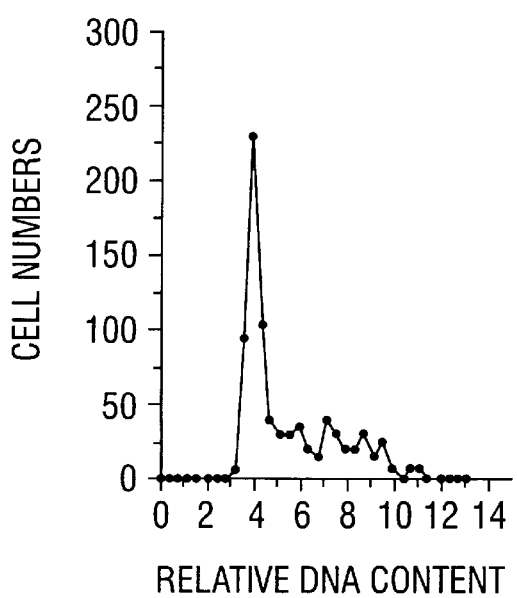

In the present invention, the following abbreviations may be used herein: MGMT: O$^6$-methylguanine-DNA methyltransferase; O$^6$-meGua: O$^6$-methylguanine; 7-meGua: 7-methylguanine; MET: methionine; HCY: homocysteine; DTT: 1, 4-dithiothreitol; BSA: bovine serum albumin; mer$^{+/-}$: MGMT expressing/deficient; GAPDH: glyceraldehyde-3-phosphate dehydrogenase.

The present invention is directed to a method of depleting methionine in the plasma of an individual in need of such treatment, comprising the steps of: administering to said individual a pharmacologically effective amount of a methionine scavenger; and treating said individual with homocystine while excluding dietary methionine, homocysteine and choline. A representative example of a methionine scavenger is 1-methionine-α-dea-γ-mercaptomethanelyase (methioninase), Hori et al., *Cancer Res.*, 56: 2116–2122. Generally, this methionine scavenging enzyme is effective when administered in an amount of from about 200 u/kg (intravenously) to about 1000 u/kg intraperitoneally. Plasma methionine depletion must be accompanied with the administration of a methionine precursor that can be converted into methionine intracellularly and thus fulfill the needs of normal cells for this essential amino acid. Homocystine (oxidesed homocysteine) was used for this purpose. In this method of the present invention, the homocystine is administered in an amount of from about 20 mg/kg to about 50 mg/kg intraperitoneally. Using this technique, one is therefore able to reduce the plasma concentration of methionine after the administration of the methionine scavenger to about 1 µM to about 7 µM. One particular advantage of this method of the present invention is that the concentration of essential amino acids and thiols such as glutathione and cysteine other than methionine is not adversely affected and that animals treated with this procedure remained healthy and active.

The present invention is also directed to a method of treating a methionine-dependent tumor in an individual in need of such treatment, comprising the steps of: administering to said individual a pharmacologically effective amount of a methionine scavenger; treating said individual with homocystine while excluding methionine, homocystine and choline from the diet; and administering to said individual a pharmacologically effective amount of an anti-neoplastic alkylating agent after the treatment has resulted in the down regulation of tumor MGMT thus sensitizing the tumor to the agent. The methionine scavenger is selected from the group consisting of 1-methionine-$\alpha$-dea-$\gamma$-mercaptomethane-lyase (methioninase). In this technique of the present invention, the methionine synthetase inhibitor is administered into experimental animals in an amount of from about 200 u/kg intravenously to about 1000 u/kg intraperitoneally every 6 to 12 hours and the homocystine is administered in an amount of from about 25 mg/kg to about 50 mg/kg twice daily. Preferably, the plasma concentration of methionine after the administration of the methioninase/homocysteine inhibitor is from about 1 $\mu$M to about 7 $\mu$M. As in the method described above, an advantage of this method of treating methionine dependent tumors is that the concentration of essential amino acids other than methionine is not adversely affected.

This method of the present invention would be generally used to treat tumors which are dependent, at least in part, on methionine, including glioblastomas, medulloblastomas, pancreatic adenocarcinomas, lung carcinomas and melanomas. In this technique of the present invention, representative examples of anti-neoplastic alkylating agent which can be used include temezolamide, procarbazine, streptozotocin, carmustine, lomustine, and related bifunctional nitrosoureas. A specific advantage of the method of the present invention is that the tumor treated using this method loses the capacity to reverse formation of $O^6$-alkylguanine adducts induced by a chemotherapeutic alkylating agent. Thus, such tumors will not display resistance to conventional chemotherapeutic agents as might otherwise do.

The following examples are given for the purpose of illustrating various embodiments of the invention and are not meant to limit the present invention in any fashion.

EXAMPLE 1
Cell Culture

NIH/3T3 from American Type Culture Collection (ATCC Rockville, Md.) was used as a negative control for methionine-dependence. SWB-40 and U-87, both mer$^-$ human anaplastic glioma cell lines, were used to determine the effect of methionine depletion on BCNU resistance by mechanisms other than those which are MGMT mediated. The effect of methionine deprivation on cell growth and MGMT levels was examined in Daoy and D-341 (human medulloblastomas), U-138 and D-263 (human glioblastomas), H-1944 (a human small cell lung carcinoma) and H-1623 (a human non-small cell lung adenocarcinoma with metastatic ability). The brain tumor cell lines were obtained either from ATCC (U-138, Daoy, U-87) or were donated by Dr H. Friedman (Department of Pediatrics, Duke University), (D-341, D-263). The lung tumor cell lines were donated by Dr. A. Gazdar (Department of Pathology, UT Southwestern) and were adapted to this medium. All cells were maintained in culture in Eagle's minimum essential medium (GIBCO) supplemented with lysine, valine and leucine (100 $\mu$M each), and with 10% dialyzed methionine free fetal bovine serum. The medium was also supplemented with non-essential amino acids (1:100 dilution of stock from GIBCO), 1 mM sodium pyruvate, sodium bicarbonate, 6.0 $\mu$M I-hydroxycobalamin, 100 $\mu$M folic acid, 0.2 mg/ml gentamicin, and either 100 $\mu$M L-methionine (MET$^+$HCY$^-$) or 200 $\mu$M D,L homocysteine thiolactone (MET$^-$HCY$^+$). Cells were plated in MET$^+$HCY$^-$ medium and were allowed to attach and grow until they reached 50% confluency ($6 \times 10^6$ per flask). Detaching cells ascertained to be dead by trypan blue exclusion were removed by changing the medium every 48 hours. Cells were then either trypsinized and reseeded in the same medium or washed with PBS and supplied with the methionine-HCY$^+$ medium. Due to extensive death in this medium, it was necessary to remove detaching dead cells on a daily basis. Cells from both media were harvested at time intervals indicated and used to measure cell cycle status and MGMT activity. Cells from either cultures ($5 \times 10^7$) were also harvested, washed with PBS and immediately frozen as a source of protein, DNA and RNA. All cells collected were live (>95%) as determined by trypan blue exclusion.

EXAMPLE 2
Staining for DNA Analysis

Trypsinized cells were washed with PBS three times and spread on slides with a cytospin centrifuge at 500 rpm for 1 minute. Slides were dipped in Fix-Rite for 1 minute, washed with water and 1 N HCl and incubated in preheated HCl at 60° C. for 15 minutes. The slides were rinsed with water, stained with Schiff's reagent for 45 minutes at room temperature, treated with two successive changes of freshly prepared sulfurous acid, rinsed well and dehydrated. Finally, slides were cover-slipped for DNA analysis. DNA content was measured by image analysis using a V-I 470 Optronics camera and Bio-Quant system IV software. Three to four hundred cells were measured in each slide and the distribution based on DNA content was determined with Lotus 123 software. A control of normal lymphocytes was used in order to assign DNA content values. MET-dependent cell cycle blocks (MDCCB) were determined according to Guo et. al (Guo, et al., 1993) using the equation:

MDCCB=% $G_1$ cells (in MET$^-$HCY$^+$)/% $G_1$ cells (in MET$^+$HCY$^-$) Where $G_1$ is the number of cells in this cell cycle phase and represented by the cells under the 1st peak of a DNA distribution graph. MDCCB numbers below 1 indicate a G2 block, while above 1 are consistent with G1 blocks.

EXAMPLE 3
MGMT Activity Measurements: Substrate Preparation

The [$^3$H]DNA substrate for measurements of MGMT activity was synthesized as follows: One mCi ethanolic solution of N-[$^3$H]methyl-N-nitrosourea (MNU) having specific activity 18.8 Ci/mmol (Amersham) was concentrated to 0.2 ml with a $N_2$ stream and mixed with 1 ml of DNA solution (5 mg) in 0.02 M 2-amino-2-methyl-1,3-propanediol at pH 10. The solution was incubated for 30 min at 37° C. in a water bath and another 30 minutes at room temperature. DNA was precipitated by adding 10% (v/v) 2.5 M sodium acetate and 3 volumes cold ethanol and allowed to stand for 18 hours at −20° C. Precipitated DNA was washed with 70% ethanol (3×) and 100% ethanol (2×) and redissolved in 3 ml 10 mM Tris, 1 mM EDTA buffer at pH 7.4.

EXAMPLE 4
MGMT Activity Measurement: Substrate Characteristics

The [$^3$H]DNA contained 29.8 μCi of radioactivity (alkylation efficiency 3%) which was distributed as 3-methyladenine 3.5%, 7-MeG 79.6%, 1-methyladenine 0.6%, O$^6$-MeG 9.0% and other adducts 7.3%. The specific activities of 7-MeG and O$^6$-MeG were calculated to be 15.8±0.8 and 16.5±0.5 Ci/mmol respectively. For all practical purposes, these were considered equal, although the specific activity of the adducts was only 86% of that reported for the MNU. Accordingly the ratio of O$^6$-MeG to 7-MeG was 0.113.

EXAMPLE 5
MGMT Measurement; Preparation of Cell Extracts

Cells were pelleted at 800 rpm and suspended in 5 volumes of 100 mM Tris.HCl containing 0.1 mM EDTA and 2 mM DAT with the pH adjusted to 7.8. Cell suspensions were freeze-thawed three times using liquid nitrogen and sonicated for 10 s (3×) using 70% maximum output. A small aliquot was removed for DNA determination. Cell debris was removed by spinning at 18,000×g for 10 minutes at 0° C. and the supernatant removed and frozen in liquid nitrogen until used. Protein was determined by the method of Bradford (Bradford, et al., 1976).

EXAMPLE 6
MGMT Assay

[$^3$H]DNA dissolved in 100 mM Tris, 0.1 mM EDTA, 2 mM DAT at pH 7.8 and containing 60 fmols of O$^6$-MeG (total dpm 24×10$^3$) was incubated with 0–500 μg of protein (depending on suspected MGMT activity) for 1 hour at 37° C. in a final volume of 500 μl. The reaction was quenched with 0.1 ml of 1 N HCl and samples were incubated for an additional 45 minutes at 70° C. Samples were cooled on ice for 1 hour, centrifuged at 14,000×g for 5 minutes, the supernatant removed and neutralized with sodium bicarbonate, and dried by lyophilization. Lyophilized samples were dissolved in 0.12 ml 0.1 M HCl, spun at 14,000×g and analyzed by HPLC using a Supelcosil-C18DB analytical column (Supelco, Inc.). Samples were eluted at a flow rate of 1.5 ml/minutes with 2% acetonitrile in 0.1 M phosphate buffer pH 3.5 (0—5 minutes) followed by a gradient of 1% acetonitrile per min (5–15 minutes). Radioactivity was monitored by fraction collection and scintillation counting. The (7-MeG and O$^6$-MeG were eluted at 4.5 and 13 minutes respectively. The ratio of radioactivity under the O$^6$-MeG over that of 7-MeG from four samples of varying protein concentration was derived and plotted against the amount of protein. The intercept of the central linear response of the curve (between ratios 0.9 and 0.3) with the x axis marks the amount of protein needed to remove 60 fmols of O$^6$-MeGua from DNA. The assay is sensitive enough to detect AGT levels as low as 5 fmols/mg protein with an error of less than 10%.

EXAMPLE 7
SDS-polyacrylamide Gel Electrophoresis and Immunoblotting

Proteins were resolved in a Bio-Rad (Richmond, Calif.) mini-gel apparatus at 200 V for 45 minutes on 0.75 mm SDS-PAGE slab gels by the method of Laemmli (Laemmli, 1970). The gels were calibrated with Bio-Rad low molecular weight standards. Proteins were transferred onto PVDF membrane (Immobilon-PTM, Millipore, Bedford, Mass.) by the method of Matsudaira (Matsudaira, 1987) using a Bio-Rad Mini trans-Blot cell for 2 hours at 140 mA. Blots were blocked with 5% BSA in 20 mM Tris pH 8.2 with 0.9% NaCl, and were probed for 2 hours with mouse monoclonal antibody MT3.1 specific for human MGMT in a buffer containing 20 mM Tris pH 8.2 0.1% BSA 0.9% NaCl, 1% normal goat serum and 5% concentrated gelatin solution (Amersham). Antibody binding was visualized with Amersham's gold labeled secondary antibody and silver enhancement using Auroprobe™ and IntenSE™ reagents (Amersham) according to manufacturer's instructions. The intensities of bands were quantitated in a photographic positive by whole band analysis on a Bio-Image Visage 110 analytical imaging instrument (Millipore).

EXAMPLE 8
DNA Probes

MGMT cDNA was derived by PCR of the cloned insert in the plasmid pKT100 (Tano, et al., 1990) using #1201 and #1211 sequencing primers (New England Biolabs, Beverly, Mass.) with a GeneAmp™ kit (Perkin Elmer Cetus, Norwalk, Conn.) using the starting parameters recommended by the manufacturer. Twenty-five cycles of amplification were carried out, with each cycle consisting of 30 seconds at 94° C., 1 minutes at 45° C. and 1 minutes at 72° C. A 772-base pairs sequence from the MGMT promoter was obtained by restriction of the plasmid pKT200 (Harris, et al., 1991) with SstI (Gibco-BRL, Gaithersburg, Md.) and PstI (New England Biolabs), and excision of the fragment from low-melting point agarose gel.

EXAMPLE 9
Northern Analysis

Total RNA was prepared from frozen cells by lysing them in RNAzol (Tel-Test, Friendswood, Tex.) according to the manufacturer's protocol. RNA (10 μg) was size fractionated in 1% agarose gels containing 2.2 M formaldehyde (Fisher, Fair Lawn, N.J.) (Sambrook, et al., 1989) and transferred to nylon membranes (Duralon-UV, Stratagene, La Jolla, Calif.) by capillary blotting. RNA was covalently attached with UV and prehybridized for 4 hours at 42° C. in 50% formamide, 5×SSPE (0.18 M sodium chloride, 0.01 M sodium phosphate, 1 mM EDTA), 5×Denhardt's solution (Sambrook, et al.,1989), 7.5% dextran sulfate, 1.5% SDS, and 200 μg/ml of sheared salmon sperm DNA. Hybridization was conducted with $^{32}$P-labeled MGMT cDNA probe for 20 hours at 42° C. Unbound probe was removed by washing membranes twice with 200 ml 2×SSC (0.015 M sodium chloride, 0.0015 M sodium citrate) for 15 minutes at room temperature, followed by washing twice with 200 ml of 0.1×SSC, 0.1% SDS for 15 minutes at 65° C. Membranes were exposed to X-Omat AR Kodak film at −70° C. and RNA was quantitated. Membranes were reprobed with GAPDH cDNA (Clontech, Palo Alto Calif.) in order to control for equal loading and transfer. After this hybridization, membranes were washed as before except that the final step was performed at 68° instead of 65° C.

EXAMPLE 10
Cytotoxicity Assays

The cytotoxicity of BCNU on cultured cells in MET$^+$HCY$^+$ and MET$^-$HCY$^+$ was measured by a modification of the method of Branch et. al. (1993) as follows: methionine-dependent cells were seeded and cultured in MET$^+$HCY$^-$ in 35 mm petri dishes until they were nearly confluent. The cells were then transferred in MET$^-$HCY$^+$ and cultured for an additional 4 to 6 days at which time cell numbers were reduced due to cell death and inhibition of mitosis. Dead cells were removed and medium was replaced on a daily basis. Following this period in MET$^-$HCY$^+$ medium, remaining live cells were washed with PBS and then treated with various concentrations of BCNU in PBS for 1 hour at 37° C. while they were still attached. Subsequently, the BCNU was removed, replaced with MET$^+$HCY$^-$ medium and cultures were incubated for an additional 4 days at 37° C. in 6% CO$_2$. At that time cells were trypsinized and counted using a Coulter-Counter (Coulter Electronics, Hialeah Fla.). The concentration of the drug that halves the growth rate of the tumor cells (IC$_{50}$), was determined from plots of BCNU concentrations versus the percent change in cell numbers as compared to untreated controls within a four day interval from treatment (Jackson, 1992). The IC$_{50}$ of BCNU on methionine-dependent cells cultured in MET$^+$HCY$^-$ or methionine independent cells cultured in either media was also determined by the same method. With such cultures, however, cell numbers originally seeded were adjusted to yield cell densities which were comparable to those of MET$^-$HCY$^+$ cultures at the time of treatment with BCNU.

EXAMPLE 11
Inhibition of Cell Proliferation by Methionine Withdrawal

Doubling times for methionine-dependent, mer$^+$ Daoy, D-341, U-138, D-263, H-1944, and H-1623 in MET$^+$HCY$^-$ were estimated from cell counting as 26, 34, 45, 42, 56, 46 hours, respectively. Doubling times for mer$^-$ U-87 and SWB-40 tumor cells and NIH-3T3 were 45, 32 and 26 hours respectively. FIG. 1 shows that with the exception of U-87 which continued to proliferate in MET$^-$HCY$^+$ the rest of the tumor lines tested were MET$^-$dependent. This was best demonstrated with Daoy, H-1623 and D-341 which were nearly eliminated 6 days following their transfer from the MET$^+$HCY$^-$ to MET$^-$HCY$^+$ medium. A less rapid or extensive reduction in cell populations within the same time period was also observed in U-138, SWB-40, D-263 and H-1944 cultures in MET$^-$HCY$^+$. After this initial cell loss, further decline of populations was observed in all tumor cell lines, although at a slower rate. The biphasic rates of cell loss in MET$^-$HCY$^+$ cultures was indicative of at least two different mechanisms of toxicity. Examination of cell cycle kinetics indicated the accumulation in late S and G$_2$ at day 2 from transfer to methionine-deficient media (FIG. 2), which was characteristic of a G$_2$ cell cycle block. Cell cycle kinetic analysis for the Daoy, U-138, H-1632, and D-341 is shown in TABLE 1.

TABLE 1

Variation Of MDCCB[a] And Mitotic Activity After Transfer Of Methionine-Dependent Tumor Cell Cultures To MET$^-$-HCY$^±$ Medium

| Cell Line | Time (days) | MDCCB | Mitotic Index % of control[b] |
|---|---|---|---|
| DAOY | 1 | 0.70 ± 0.10[c] | 51 ± 6[c] |
|  | 2 | 0.45 ± 0.11 | 24 ± 4 |
|  | 3 | 0.89 ± 0.08 | 12 ± 4 |
|  | 4 | 1.10 ± 0.06 | 3 ± 2 |
|  | 5 | 1.62 ± 0.11 | 0 |
|  | 6 | 1.68 ± 0.13 | 0 |
| U-138 | 2 | 0.85 ± 0.09 | 38 ± 11 |
|  | 4 | 0.61 ± 0.08 | 21 ± 7 |
|  | 6 | 0.99 ± 0.12 | 6 ± 3 |
|  | 8 | 1.05 ± 0.09 | 0 |
|  | 10 | 1.45 ± 0.09 | 0 |
| H-1623 | 1 | 0.42 ± 0.06 | 27 ± 5 |
|  | 2 | 0.88 ± 0.04 | 13 ± 3 |
|  | 4 | 1.35 ± 0.12 | 5 ± 2 |
|  | 6 | 1.57 ± 0.11 | 0 |
| D-341 | 1 | 0.66 ± 0.08 | 49 ± 11 |
|  | 2 | 0.45 ± 0.06 | 12 ± 4 |
|  | 4 | 0.89 ± 0.09 | 0 |
|  | 6 | 1.06 ± 0.11 | 0 |
|  | 8 | 1.31 ± 0.12 | 0 |

[a]MDCCB = methionine-dependent cell cycle blocks. Numbers <1.0 show accumulation of cells in G2, while >1 demonstrate a G1 block.
[b]Mitotic indexes (mitosis per 1000 cells) for Daoy, U-138, H-1623 and D-341 in MET$^+$HCY$^-$ were 49, 39, 52 and 67 respectively.
[c]Mean of three of three experiments ± standard deviation.

Methionine-dependent G2 cell cycle blocks (MDCCB<0.8) were observed in all the of these four lines, but they were not detectable in H-1944, SWB-40 and D-263, which were moderately to weakly dependent on methionine. A G2 block was imposed earlier in H-1623, D-341 and Daoy than in U-138 and was generally followed by a massive detachment and death of cells (FIG. 1), and a concomitant increase of the MDCCB (TABLE 1). Following the G2 block and elimination of G2 arrested cells, the mitotic index declined rapidly by more than an order of magnitude below the control value as the MDCCB number increased above 1, indicating that surviving cells did not cycle and were most probably checked at G$_1$. MDCCB fluctuations consistent with G2 or G$_1$ blocks were not found in NIH-3T3 or U-87 which were not methionine-dependent and proliferated in MET$^-$HCY$^+$. Cell cultures of methionine-dependent cells could be rescued, even after elimination of more than 95% of the original cell population, by replenishing methionine in the medium. Karyotypic analysis before methionine depletion and also 48 hours after the repletion of methionine in a Daoy culture deprived of methionine for ten days, indicated that no additional chromosomal aberrations or selection of a resistant cell population were introduced by this treatment. In all cell lines tested, repletion of methionine in the medium resulted in the recovery of both cell proliferation capacity and base line MGMT activity. In Daoy, recovery of the MGMT activity was not complete 48 hrs (65% of the base line) from repletion of methionine following a 10 day culture period in HCY. At that time cells had recovered their ability to divide and proliferated with a doubling time of 22 hours.

EXAMPLE 12

Reduction of MGMT Activity in Tumor Cells By Methionine Depletion

The native MGMT activities of the cell lines tested here are shown in TABLE 2. These activities were not affected by serum withdrawal and the associated inhibition of growth for up to 72 hours, and they were not dependent on the state of confluency of the culture (data not shown). A cell cycle dependent regulation of MGMT activity, previously suggested (Dunn et al., 1986) by serum starvation synchronization, was also not evident in these lines. However, MGMT activities were dependent on the presence of methionine in the culture medium (TABLE 2).

TABLE 2

Time Dependence Of MGMT Activity In MET⁻-HCY⁺Cultures

| Cell Line | Time[a] | MGMT[b] | Cell Line | Time[a] | MGMT[b] |
|---|---|---|---|---|---|
| DAOY | 0 | 383 ± 41[c] | H-1623 | 0 | 880 ± 51 |
|  | 2 | 85 ± 9 |  | 2 | 326 ± 62 |
|  | 4 | 61 ± 5 |  | 4 | 132 ± 9 |
|  | 6 | 32 ± 4 |  | 6 | 51 ± 13 |
|  | 8 | 35 ± 3 |  | 8 | 41 ± 12 |
|  | 10 | 33 ± 5 |  |  |  |
| U-138 | 0 | 384 ± 35 | H-1944 | 0 | 328 ± 11 |
|  | 2 | 140 ± 13 |  | 2 | 263 ± 28 |
|  | 4 | 85 ± 9 |  | 4 | 143 ± 17 |
|  | 6 | 33 ± 4 |  | 6 | 75 ± 5 |
|  | 8 | 21 ± 4 |  | 8 | 48 ± 5 |
|  | 10 | 25 ± 3 |  | 10 | 42 ± 5 |
| D-341 | 0 | 361 ± 18 | NIH3T3 | 0 | 236 ± 33 |
|  | 2 | 139 ± 15 |  | 2 | 287 ± 18 |
|  | 4 | 63 ± 8 |  | 4 | 285 ± 32 |
|  | 6 | 35 ± 4 |  | 6 | 291 ± 43 |
|  | 8 | 33 ± 4 |  | 8 | 311 ± 58 |

[a]Days after replacing MET⁺ HCY⁻ with MET⁻ HCY⁺ medium.
[b]fmol/mg protein.
[c]Standard deviation from three determinations.

Figure 3:
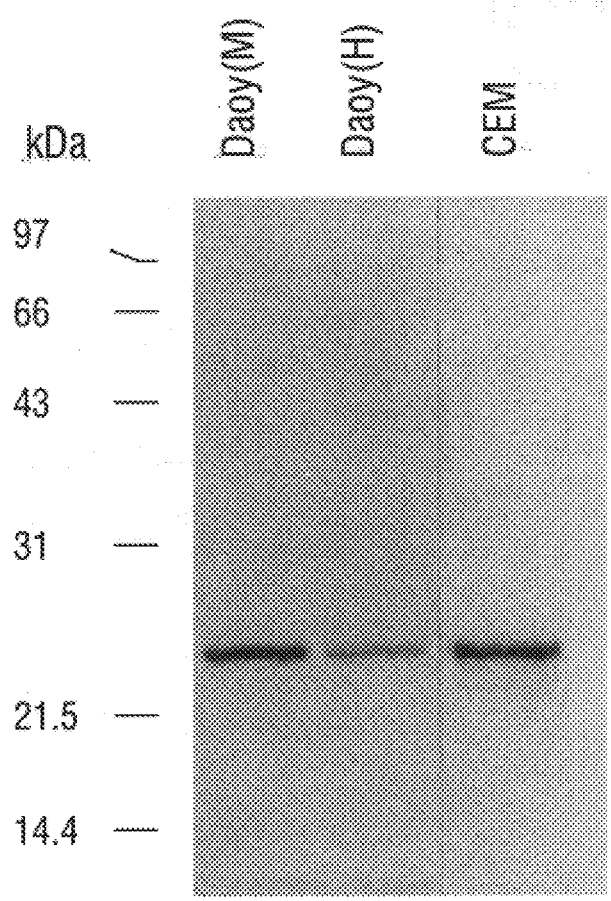
FIG. 3 shows the immunoblot analysis of MGMT protein in Daoy cell line cultured in either MET$^+$HCY$^-$ (M), or in MET$^-$HCY$^+$ (H) media. Twenty µg of extract protein was electrophoresed in a 12% SDS polyacrylamide gel. Proteins were electroblotted onto a PVDF membrane which was probed with monoclonal antibody MT3.1 specific for human MGMT. MGMT in the human leukemic lymphoblast line CEM-CCRF is shown as control.
Figure 4:
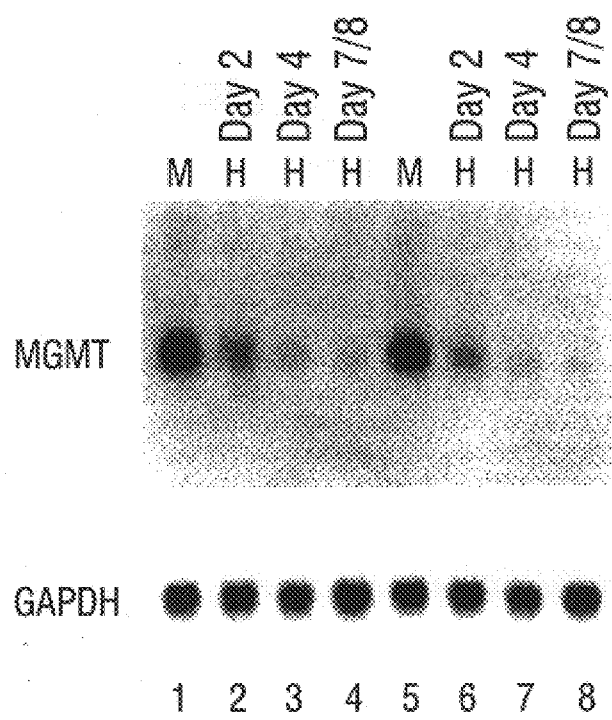
FIG. 4 shows the northern analysis of MGMT mRNA expression in Daoy cultured in either MET$^+$HCY$^-$ (M), or in MET$^-$HCY$^+$ (H). Twenty µg of total RNA from a MET$^+$ HCY$^-$ culture and from cultures deprived of methionine (MET$^-$HCY$^+$) for 2, 4 or 7/8 days respectively were subjected to electrophoresis, transferred to a nylon membrane, and probed with $^{32}$P-labeled human MGMT cDNA (upper panel). Reprobing the membrane with $^{32}$P-labeled GAPDH cDNA (lower panel) demonstrated comparable loading for all samples. Lanes 1–4 and 5–8 represent duplicate Northern analyses.
Figure 5B:
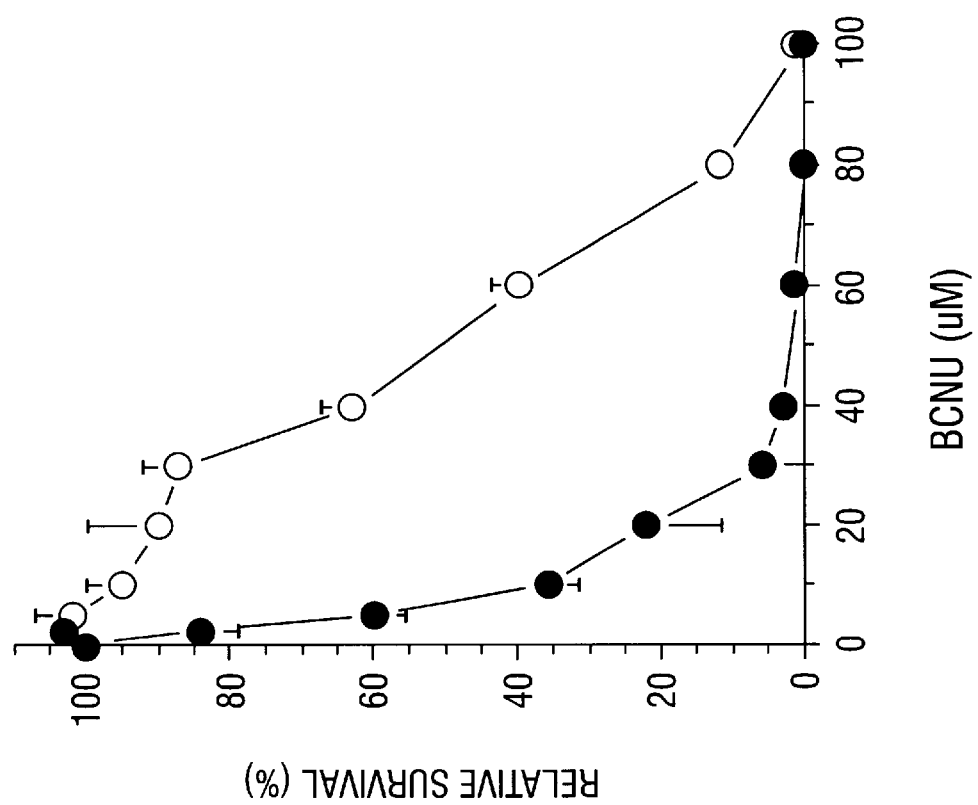
FIG. 5 shows the effect of methionine depletion on the sensitivity of the mer$^-$ SWB-40 (FIG. 5A) and the mer$^+$ Daoy (FIG. 5B) cell lines to BCNU. Cells previously cultured in MET$^+$HCY$^-$ (o) or in MET$^-$HCY$^+$ (•) for 4 (Daoy) or 6 (SWB-40) days were exposed to BCNU for 1 hour at 37° C. and subsequently cultured in MET$^+$HCY$^-$ medium. Live cell populations were determined at day 4 after BCNU treatment in expanding cultures and plotted against BCNU concentrations. Cell numbers were compared with those of their respective control (no BCNU) to determine BCNU-induced growth inhibition and death.
Figure 5A:
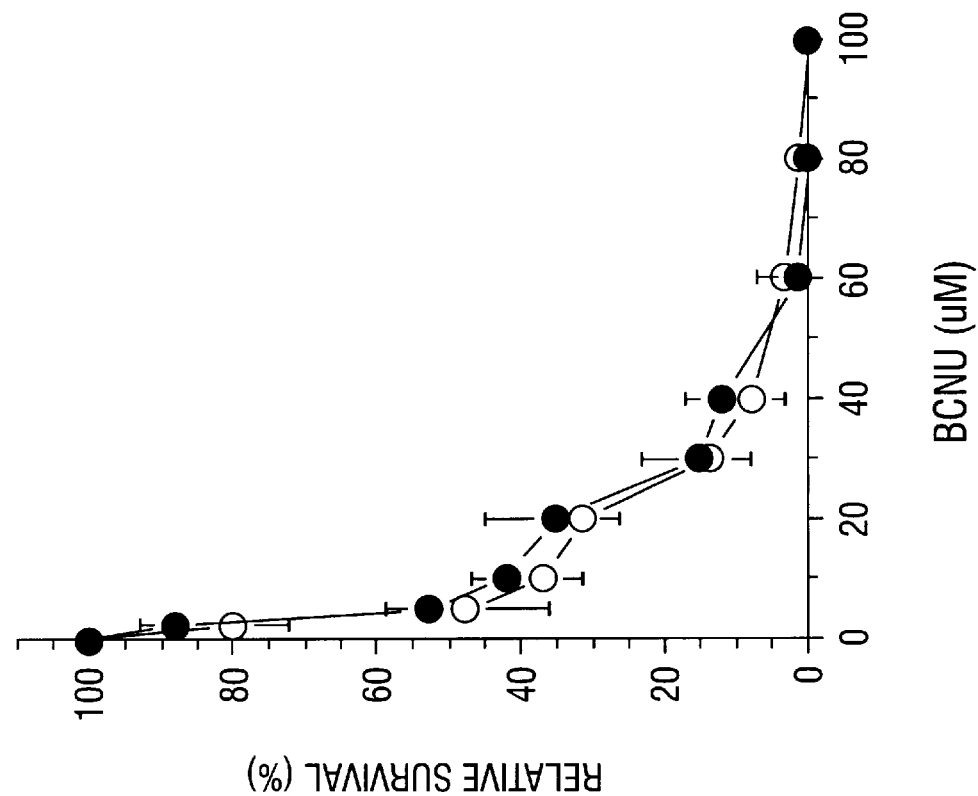

With the exception of NIH-3T3 cells, which were not methionine-dependent, MGMT activity declined with a half-life ranging from 24 to 48 hours after cells were transferred to MET⁻HCY⁺ media and reached a nadir of 25 to 40 fmol/mg protein in all the lines tested. Levels of MGMT activity remained low in methionine-dependent cells as long as such cells remained alive in the MET⁻HCY⁺ medium. In Daoy, the decline in the MGMT activity in MET⁻HCY⁺ was due to the reduction of MGMT protein (FIG. 3). The amount of MGMT protein determined by densitometric scanning six days after culturing in MET⁻HCY⁺ was reduced by eight-fold, which was similar to the decline of MGMT activity. Northern analysis (FIG. 4) indicated that the reduction of the protein and activity was reflected by a similar reduction of mRNA without notable reduction of mRNA for GAPDH, another "housekeeping" protein. Reduction of the MGMT mRNA was notable 48 hours after transfer to MET⁻HCY⁺ medium and further declined to levels which were barely detectable a week after methionine deprivation. The above suggests that methionine deprivation affects MGMT transcription or mRNA stability, and probably not MGMT protein translation or stability. Downregulation of MGMT expression by methionine deprivation could be theoretically related to changes in methylation of cytosine in key positions of the MGMT gene and promoter due to the decline of the capacity of cells to transmethylate when cultured in a homocysteine medium.

Recent studies have shown that cytosine methylation influences MGMT gene expression (von Wronski et al., 1992; Wang et al., 1992; Costello et al., 1994). Methylation of the MGMT promoter is associated with loss of gene expression, while methylation of the gene itself appears to enhance its expression. Specifically methylation in the Sma I restriction site (-69) of the MGMT promotor has been found only in Mer(-) tumor cell lines (von Wronski et al., 1992). On the other hand, 5-azacytidine induced methylation of the body of the gene at HpaII sensitive sites results in a substantial increase of the MGMT activity in some tumor cell lines (von Wronski et al., 1994).

Figure 6A:
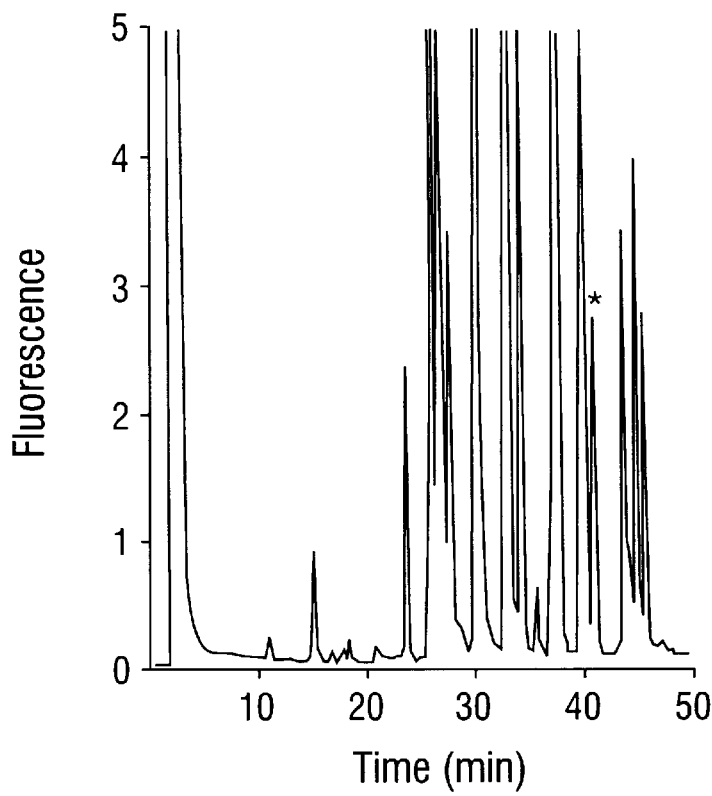
FIG. 6 shows an amino acid analysis in plasma of nude mice fed a met+hcy−chl− (A) or met−hcy+chl− (B) diets for 7 days. The effect of injecting a single dose of 1000 u/kg methioninase on methionine levels in plasma of met$^+$hcy$^-$ chl$^-$ (C) or met$^-$ hcy$^+$chl$^-$ (D) fed mice 6 hours after treatment is also shown. The methionine peak is marked with an asterik.
Figure 6B:
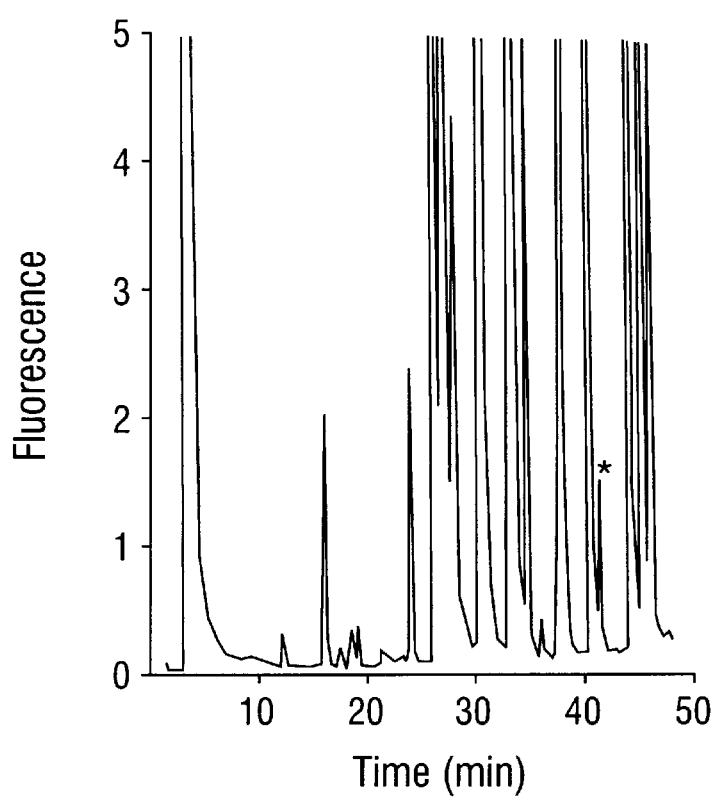
Figure 6C:
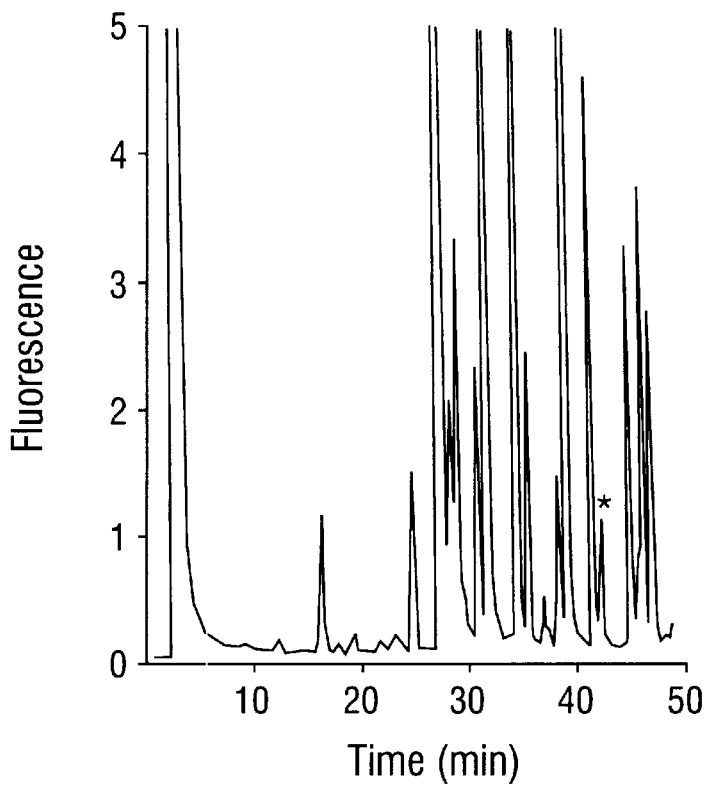
Figure 6D:
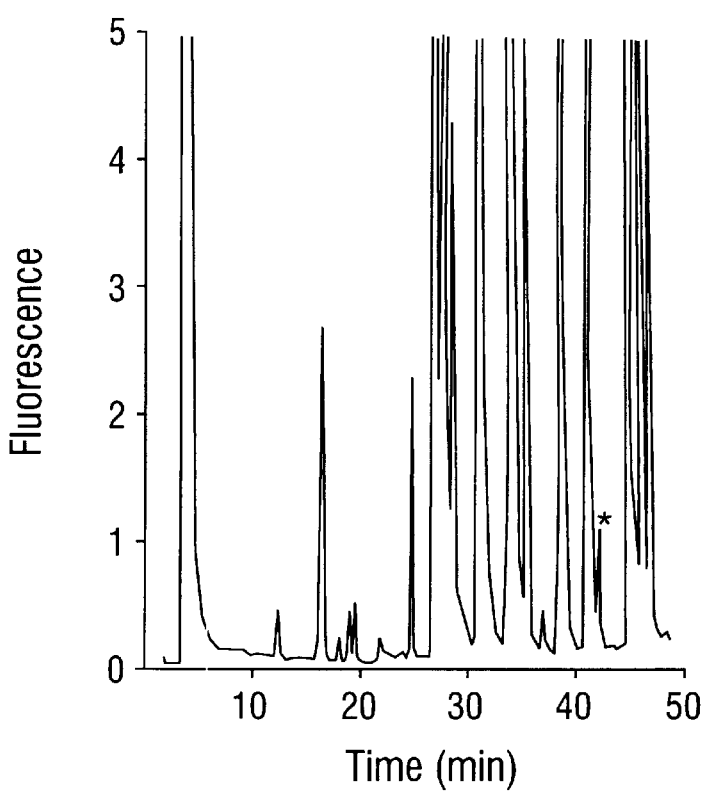
Figure 7A:
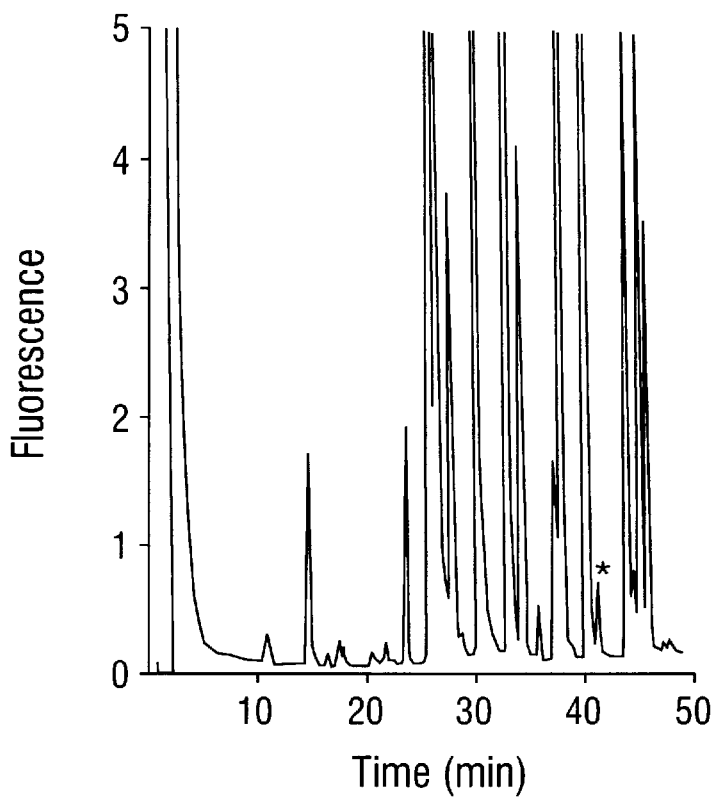
FIG. 7A: homocysteine thiolactone.
Figure 7B:
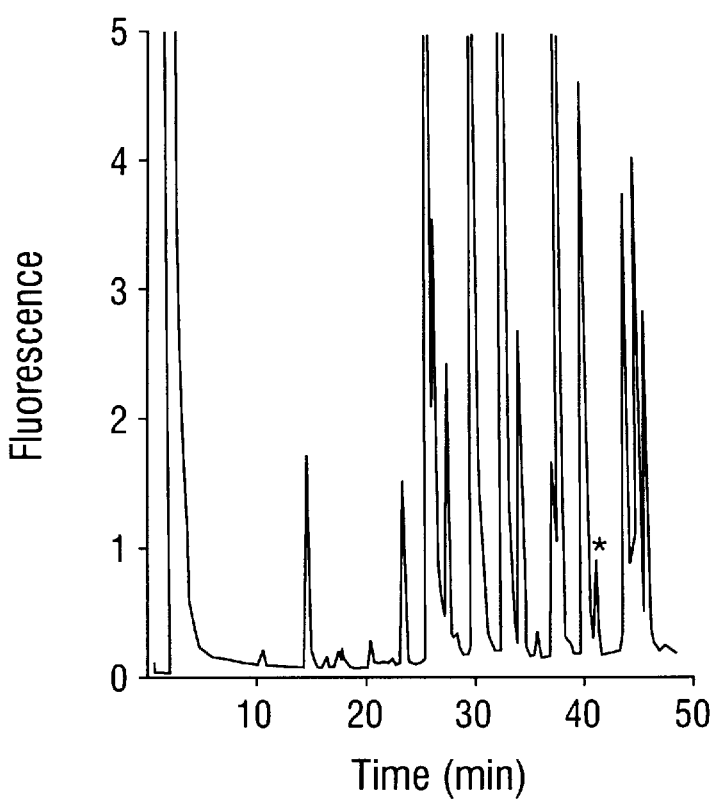
FIG. 7B: homocysteine thiolactone+methioninase.
Figure 7C:
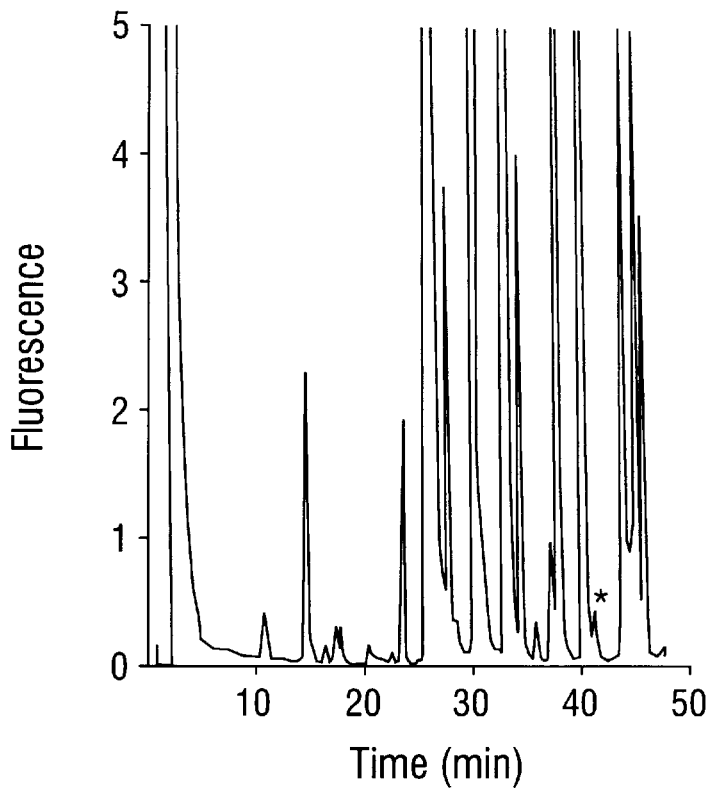
FIG. 7C: homocystine.
Figure 7D:
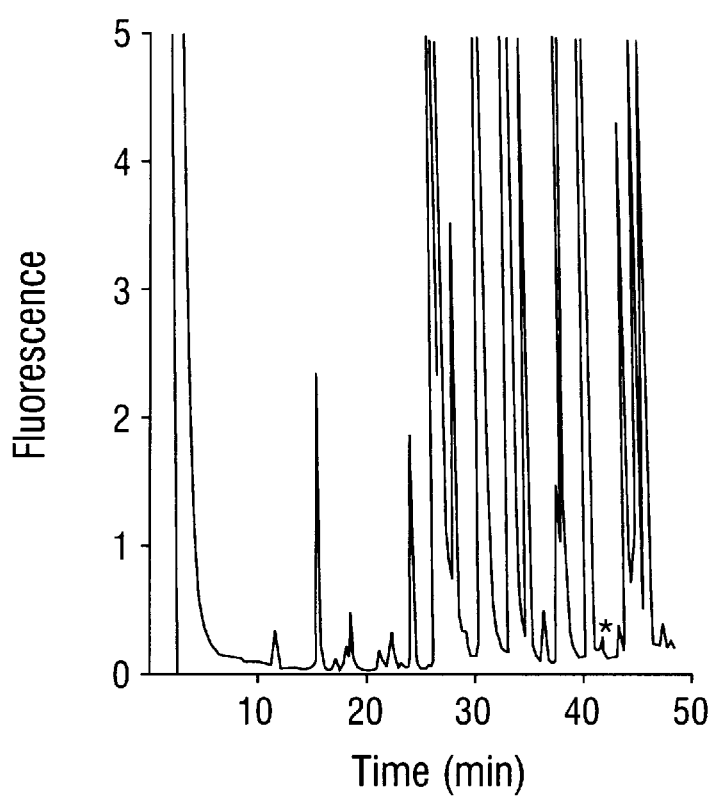
FIG. 7D: homocystin+methioninase. All animals were killed 6 hours after the injection of the methionine precursor.

EXAMPLE 13
Potentiation of the Toxicity of Nitrosoureas by Methionine Depletion The mer⁺ Daoy line was resistant to BCNU in MET⁺ HCY⁻ with an IC$_{50}$ of 45 $\mu$M. Such resistance was compromised and the IC$_{50}$ was reduced to approximately 5 $\mu$M when cells were cultured in MET⁻HCY⁺ for 4 days prior to the exposure to BCNU (FIG. 6A). In comparison, the resistance of the mer⁻, methionine-dependent SWB-40 to BCNU was not affected by methionine depletion (FIG. 6B). The comparable response of mer⁺ Daoy and mer⁻ SWB-40 to BCNU in MET⁻HCY⁺, and the demonstrated association between BCNU sensitivity and MGMT activity in Daoy suggests that this line owes its resistance to alkylating agents to the high levels of MGMT reserves. On the other hand, the marginal effect of methionine deprivation on the resistance of SWB-40 to BCNU suggests that downregulation of MGMT activity is probably the major pathway for the loss of resistance to BCNU and to related alkylating agents in association with the methionine-dependence phenotype. An extensive correlation between the downregulation of MGMT activity by methionine deprivation and the sensitization to BCNU was demonstrated with several mer⁺, methionine-dependent cell lines (TABLE 3)

TABLE 3

Sensitization Of Methionine-Dependent Tumor Cells To BCNU By Methionine Withdrawal

| Cell Line | Remaining MGMT[a] | IC$_{50}$ (MET)[b] | IC$_{50}$ (HCY) |
|---|---|---|---|
| Daoy | 8.6 | 45 | 5 |
| U-138 | 6.5 | 50 | 10 |
| D-341 | 9.1 | 65 | 10 |
| H-1623 | 4.6 | 90 | 10 |
| H-1944 | 12.8 | 65 | 10 |
| U-87[c] | nd | 15 | 15 |
| SW-40[c] | nd | 10 | 15 |
| NIH-3T3[d] | 131.8 | 35 | 40 |

[a]Percent MGMT activity remaining after exhaustive deprivation of exogenous methionine.
[b]Concentration ($\mu$M) of BCNU needed to reduce relative survival by 50% four days following 1 hour incubation with the drug.
[c]mer - lines, not detectable (nd) MGMT.
[d]control mer +, methionine-independent cell line.

Tumors have high methionine requirements due to accelerated protein synthesis and transmethylation reactions to yield S-adenosylmethionine, serine, sarcosine, glycine and various phospholipids (Mineura et al., 1993; Kubota et al., 1995). Twenty percent of human tumors are estimated to be absolutely dependent of methionine and cannot utilize homocysteine to either proliferate or survive (Guo, 1993). A greater percentage is expected to be moderately to weakly dependent on methionine and respond to some extent to methionine-deprivation (Hoshiya et al., 1995). In this regard methionine-deprivation is an interesting approach to therapy of a variety of tumors assuming that reduction of plasma methionine below the threshold needed to suppress cell proliferation in the tumor can be achieved. The exogenous methionine requirement of methionine-dependent tumor cell lines varies (Halpern, et al., 1974; Hoffman, 1976; Breillout, et al., 1987). The present invention shows that prolonged reduction of plasma methionine, can be non-toxic in animals if homocysteine is supplemented to supply normal tissues with a methionine precursor. Thus an eighty percent reduction of plasma methionine has been obtained in athymic mice fed a methionine-free diet. Further reduction (~95%) can be achieved with the use of L-methionine-α-deamino-γ-mercaptomethane lyase, also known as methioninase (Lishko et al., 1993), an enzyme that has been recently cloned and mass produced (Hori et al., 1996). A combination of methionine-depleting diets and methioninase could theoretically cause a decrease in plasma methionine to less than 5 $\mu$M, which is the threshold for supporting cell proliferation in all methionine-dependent tumor cell cultures examined.

Three out of eight tumors tested here are strongly dependent on methionine and are rapidly and nearly eradicated, mainly as the result of G2 blocks induced by methionine-deprivation. The rest of the tumors tested, including all gliomas, resisted methionine-starvation (in the presence of HCY) and were able to survive for several weeks and resume growth when methionine was repleated. Prolonged survival, possibly due to G1 cell cycle blocks of methionine-dependent tumor cells is expected to be a major problem in any effort to eradicate tumors based entirely on methionine-depleting regimens. In this regard, although methionine-depletion may be useful in replacing toxic chemotherapeutic treatments, its greater application could be in conjunction with currently used chemotherapeutic agents.

A major mechanism of resistance of cells to genotoxic injury, particularly to the formation of the toxic and mutagenic $O^6$-alkylguanine DNA adducts and to subsequent lethal DNA crosslinks, is mediated by the DNA repair protein MGMT. This protein, which reverses formation of $O^6$-alkylguanine adducts, including those with the potential to react with DNA bases of the opposite strand and form crosslinks, is abundant in more than eighty percent of the human tumors, rendering them resistant to a variety of genotoxic alkylating chemotherapeutic agents (Day, et al., 1980; Tsujimura, et al., 1987). In many cases, levels of MGMT activity in tumor tissue are well above that of the normal surrounding tissue or of other vital tissues (Gerson, et al., 1985). This is believed to be the main reason for the poor therapeutic index of many chemotherapeutic genotoxic drugs that alkylate the $O^6$-position of guanine used in chemotherapy. Significant increase in the efficacy of alkylating chemotherapeutic drugs, such as BCNU, against MGMT positive tumors has been obtained with the prior depletion of MGMT activity both in tumor and in normal tissue by $O^6$-benzylguanine and its analogs (Dolan, et al., 1993; Schold, et al., 1996). Depletion of MGMT in animals treated with $O^6$-benzylguanine analogs is effective provided the inhibitor and its active metabolites are present in adequate concentrations to sustain destruction of newly synthesized MGMT (Kokkinakis, et al., 1996). Since MGMT inhibitors inactivate only existing protein and have no effect on the transcription or translation of the stable MGMT message, MGMT activity appears immediately after clearance of the inhibitor due to continuous translation of persisting MGMT mRNA. An even greater increase in the efficacy of BCNU and similar genotoxic drugs that kill primarily because of $O^6$-alkylguanine adducts, can be achieved by depleting both the MGMT protein and its mRNA only in the tumor while leaving normal tissues unaffected. Theoretically this can be accomplished in tumors that possess both the methionine dependence and mer+ phenotypes by methionine-depleting regimens.

Selective depletion of both the MGMT protein and its mRNA can be imposed on tumor cells by methionine deprivation. Depletion of the activity and most probably of the protein in Daoy, U-138, D-341, and H-1623 follows first order kinetics with half lives varying between 36 and 48 hours. In H-1944 and D-263 which are weakly dependent on methionine, a lag period of approximately 48 hours precedes such decline of activity. The detection of MGMT mRNA in Daoy, 8 days after methionine-withdrawal suggests that transcription of the MGMT gene is not completely silenced in a methionine-depleted state. Persistence of MGMT mRNA for that length of time without new synthesis is unlikely in spite of the reported stability of the MGMT message in several tumor cells lines (Kroes and Erickson, 1995). Low levels of MGMT found in methionine$^-$HCY$^+$ for several days after reaching a nadir further demonstrate the slow rate of basal transcription of this gene by cells which are apparently blocked in $G_1$. In the simplest scenario methionine withdrawal inhibits transcription, but has no effect on the stability of mRNA and protein. A gradually declining MGMT activity therefore reflects the difference between degradation of the protein with a half-life of approximately 20 hours (Brent, 1991) and translation of pre-existing mRNA which is also on a decline with a half-life of approximately 12 hours (Kroes and Erickson, 1995). Resynthesis of protein, mainly from translation of pre-existing mRNA, may influence the kinetics of MGMT decline by increasing the apparent half lives of the MGMT activity from the expected 20 hours up to 48 hours depending on the tumor line. A lag period in the decline of MGMT activity observed in H-1944 is probably the result of the ability of this cell line to utilize homocysteine and maintain higher levels of endogenous methionine than Daoy (data not shown).

The mechanism of downregulation of MGMT activity by methionine deprivation could potentially involve changes in the methylation of the gene. Such changes particularly at the promoter region of the MGMT gene have already been recognized as having an intimate association with cellular levels in MGMT activity. Thus a direct correlation between methylation in the body of the gene and MGMT expression has been observed (Pieper et al. 1991, von Wronski and Brent, 1994; Harris, et al., 1994), whereas methylation at the 5' promotor region has been associated with complete suppression of the gene (von Wronski, et al., 1992; von Wronski, 1994). Consistent with the latter correlation, cells expressing high levels of MGMT, such as Daoy and U-138 are not methylated at the Sma I site of the promoter. It is not surprising that the Sma I site remained methylation free under conditions of methionine deprivation, although such methylation would be consistent with the observed MGMT suppression. It is still possible that methylation of the promoter region at other sites could be involved in transcriptional suppression since a number of sites with such potential have been identified in tumor cells (Qian et al. 1996). However, regulation of MGMT activity by hypermethylation of the promoter is not expected to occur in a methionine deficient state, especially in the presence of high levels of homocysteine which could result in the accumulation of S-adenosylhomocysteine and consequently in the inhibition of DNA methylation and other transmethylation reactions (Johnson and Aswad, 1993). If methionine deprivation regulates MGMT activity by changing the methylation status of the gene, it would be expected that such regulation would be due to the hypomethylation of the downstream region rather than the methylation of the promoter. The absence of changes in the methylation of the body of the gene indicates that either methylation is not involved in the downregulation of MGMT by methionine deprivation, or changes of the status of methylation are not detected by the methodology used. If methylation of CpG islands is not involved in the downregulation of MGMT activity in methionine-dependent tumors by methionine deprivation it may be due to changes in chromatin structure or transacting factors by mechanisms not yet identified.

The downregulation of MGMT by methionine deprivation mer$^+$, methionine-dependent tumor cells indicates that methionine-dependent tumors are susceptible to methionine deprivation not only because of cell cycle blocks, but at the same time are sensitized to those alkylating agents that owe their toxicity to their ability to form alkyl adducts at the $O^6$-position of guanine. The present invention indicates that the reduction of MGMT activity is not strictly dependent on the degree of sensitivity of the tumor to methionine deprivation. Tumor cells which are moderately methionine-dependent and resist methionine withdrawal, such as U-138, lose their MGMT activity nearly as fast as fully methionine-dependent lines, such as the H-1623 and Daoy. This is particularly important in vivo where methionine levels cannot be indefinitely suppressed to near zero levels. Thus methionine depleting regimens, dietary or enzymatic, could be used to arrest or reverse tumor growth long enough to suppress MGMT activity. Elimination of a substantial portion of the tumor mass due to G2 blocks may facilitate further treatment of the tumor, but it is not an absolute requirement for the employment of chemotherapy aiming to kill cells sensitized to DNA damage. Additional mechanisms of resistance may also have been compromised by the lack of methionine which could explain the reported susceptibility of methionine-dependent cells to the combination of methionine depletion with antineoplastic drug other than alkylating agents. These results support the use of methionine depletion regimens in combination with genotoxic drugs for the treatment of methionine-dependent, mer$^+$ tumors.

EXAMPLE 14

In Vivo Effects of Methionine Availability on Tumor Growth and MGMT Activity

Several diets designed to limit plasma methionine were used. Two of the three diets employed were deficient in choline and contained either methionine (met+hcy$^-$chl$^-$) or DL homocystine in place of methionine (met$^-$hcy$^+$chl$^-$). These diets support similar rates of animal growth and have no ill side effects on internal organ function and integrity. The third diet was also deficient in methionine, homocystine, and choline and did not support growth. This third diet caused severe deterioration of hepatic and pancreatic tissues and led to death within 10 to 15 days from implementation.

Plasma methionine varies between 60 and 100 μM in nude mice fed a basal diet (Harlan Teklad Lab. Diet). However, methionine levels are significantly lower in the plasma of animals fed synthetic diets. As shown in TABLE 4, a transition from a basal diet to a met$^+$hcy$^-$chl$^-$ diet results in a 43% reduction in plasma methionine. Further reduction was observed with a met$^-$hcy$^+$chl$^-$ diet. Even more dramatic changes in plasma methionine were observed in animals fed the met$^-$hcy$^-$chl$^-$ diet for 24 hours following a week long adaptation to the lack of dietary methionine by feeding the met$^+$hcy$^-$chl$^-$ diet. On the other hand, when dietary methionine was limited, tissues with high methionine requirements, and possibly tumors may be undersupplied with methionine by the circulation. In animals fed a basal diet, levels of methionine in plasma, liver and tumor were similar. This was to be expected by an oversupply of this amino acid.

TABLE 4

Synthetic, methionine restricted diets suppress levels of methionine in plasma and liver of nude mice

| Diet | Time (Days) | Blood | Liver | Tumor |
|---|---|---|---|---|
| basal | >7 | 89 ± 13 | 85 ± 11 | — |
| basal | >7 | 71 ± 8 | 90 ± 12 | 135 ± 19 |
| met$^+$hcy$^-$ch$^-$ | 7 | 51 ± 8 | 23 ± 4 | — |

TABLE 4-continued

Synthetic, methionine restricted diets suppress levels of methionine in plasma and liver of nude mice

| Diet | Time (Days) | Blood | Liver | Tumor |
|---|---|---|---|---|
| met$^-$hcy$^+$ch$^-$ | 7 | 42 ± 7 | 26 ± 7 | — |
| met$^-$hcy$^-$ch$^-$ | 0.5 | 30 ± 6 | 17 ± 4 | — |
| met$^-$hcy$^-$ch$^-$ | 1.0 | 17 ± 3 | 16 ± 4 | — |

[1]Tumors were implanted in animals receiving a complete, non-synthetic commercial diet. Animals kept on synthetic diets did not have tumors.

As shown in FIG. 6 and summarized in TABLE 5, an intraperitoneal injection of 1000 u/kg methioninase markedly reduces plasma levels of methionine in mice fed either a met$^+$hcy$^-$chl$^-$ or a met$^-$hcy$^+$chl$^-$ diet (FIG. 6). The lowest possible level of methionine that can be achieved with the use of a growth sustaining synthetic diet and methioninase is about 15 μM. Restriction of methionine by such means does not result in marked changes of homocysteine, cysteine and glutathione levels in plasma (TABLE 5).

TABLE 5

Dietary and pharmacological manipulation of plasma methionine does not cause depletion of cysteine and glutathione in plasma

| Diet | MET precursor | METH. | CYS μM | HCY μM | MET μM | GSH μM |
|---|---|---|---|---|---|---|
| met$^+$hcy$^-$chl$^-$ | none | − | 95 ± 8 | 15 ± 3 | 54 ± 5 | 61 ± 11 |
| met$^+$hcy$^-$chl$^-$ | none | + | 82 ± 16 | 20 ± 4 | 20 ± 2 | 59 ± 7 |
| met$^-$hcy$^-$chl$^-$ | none | − | 145 ± 19 | 32 ± 6 | 17 ± 2 | 81 ± 8 |
| met$^-$hcy$^-$chl$^-$ | none | + | 118 ± 11 | 12 ± 1 | 21 ± 3 | 41 ± 3 |
| met$^-$hcy$^-$chl$^-$ | hcy-thio-lactone | − | 100 ± 13 | 20 ± 3 | 12 ± 3 | 81 ± 11 |
| met$^-$hcy$^-$chl$^-$ | hcy-thio-lactone | + | 110 ± 2 | 17 ± 2 | 17 ± 4 | 44 ± 6 |
| met$^-$hcy$^-$chl$^-$ | homo-cystine | − | 100 ± 4 | 17 ± 2 | 6 ± 2 | 56 ± 8 |
| met$^-$hcy$^-$chl$^-$ | homo-cystine | + | 75 ± 8 | 12 ± 3 | <1 | 37 ± 4 |

[1]Levels of total thiols in circulation 8 hours after injection (ip) of met precursor and 6 hours after treatment with methioninase. Mean of 3 determinations ± SD. MET precursor was 50 mg/kg; methioninase (abbreviated METH.) was 1000k U/kg.

Further reduction of plasma methionine can be achieved with the use of a diet free of methionine, homocysteine and choline if such dietary manipulation is accompanied by daily injections of 50 mg/kg homocystine (TABLE 5). Methionine can be practically eliminated from plasma if animals fed a met$^+$hcy$^-$chl$^-$ diet and receiving homocystine ip were also treated with methioninase twice per day (FIG. 7, TABLE 5). Measurements of other plasma thiols (TABLE 5) demonstrate that cysteine, homocysteine and glutathione levels, although they are somewhat reduced in plasma as a result of such treatment, can still remain near physiological levels.

EXAMPLE 15

Tumor Growth in Animals Fed Methionine-Depleting Diets

Figure 8:
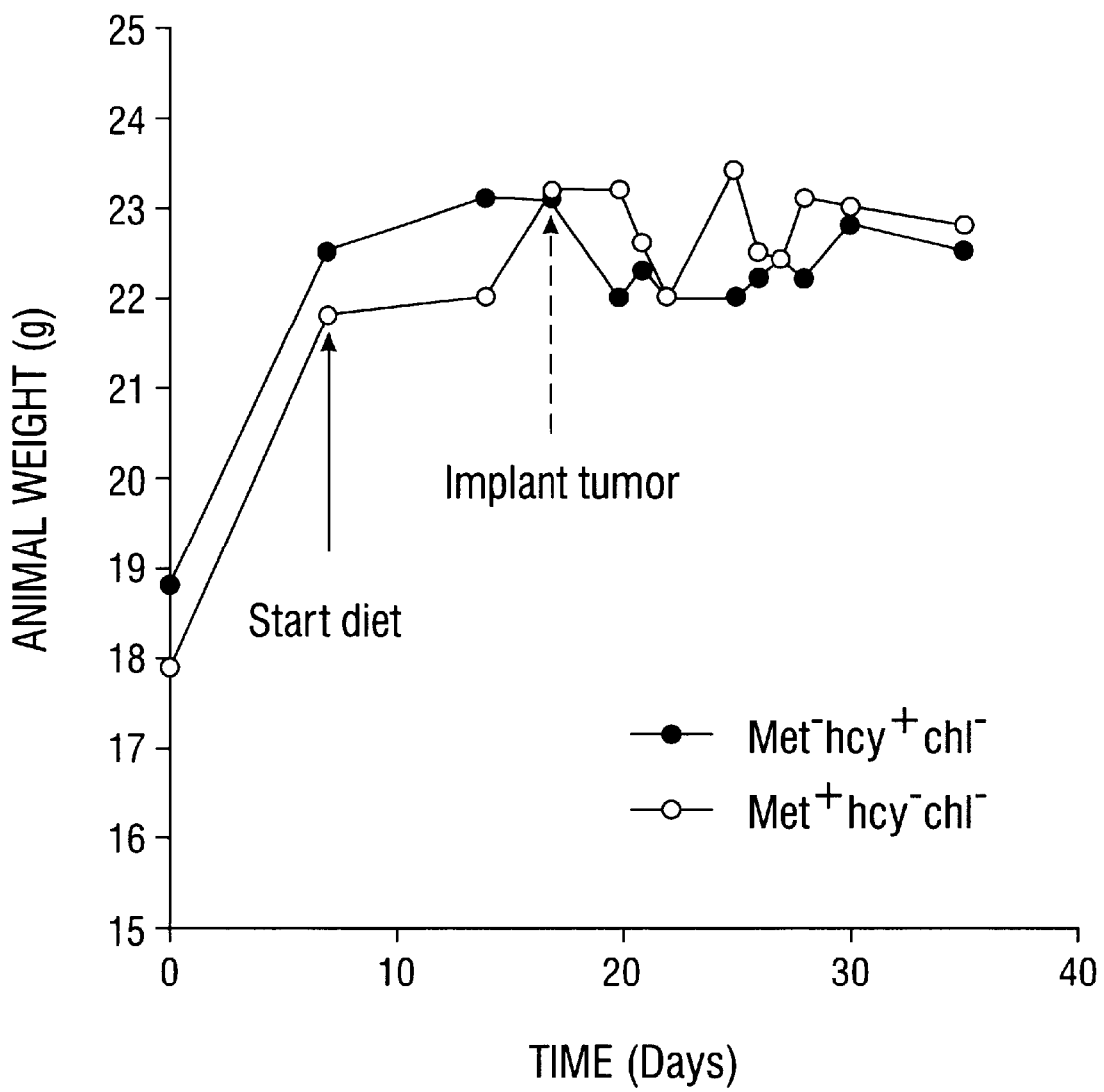
FIG. 8 shows the effect of met$^-$hcy$^+$chl$^-$ or met+hcy$^-$chl$^-$ diet on growth of tumor bearing athymic mice. Omission of MET or choline (chl) does not affect growth.

Twenty athymic mice were divided into two groups and fed met$^+$hcy$^-$chl$^-$ or met$^-$hcy$^+$chl$^-$ diets, respectively. As shown in FIG. 8, the animals maintained their weight under both of these dietary regimens. Tumor implantation had no effect on animals maintaining a normal weight range that was dependent on the source of methionine.

EXAMPLE 16

Effect of Methionine Depletion on Tumor MGMT Levels

Figure 9:
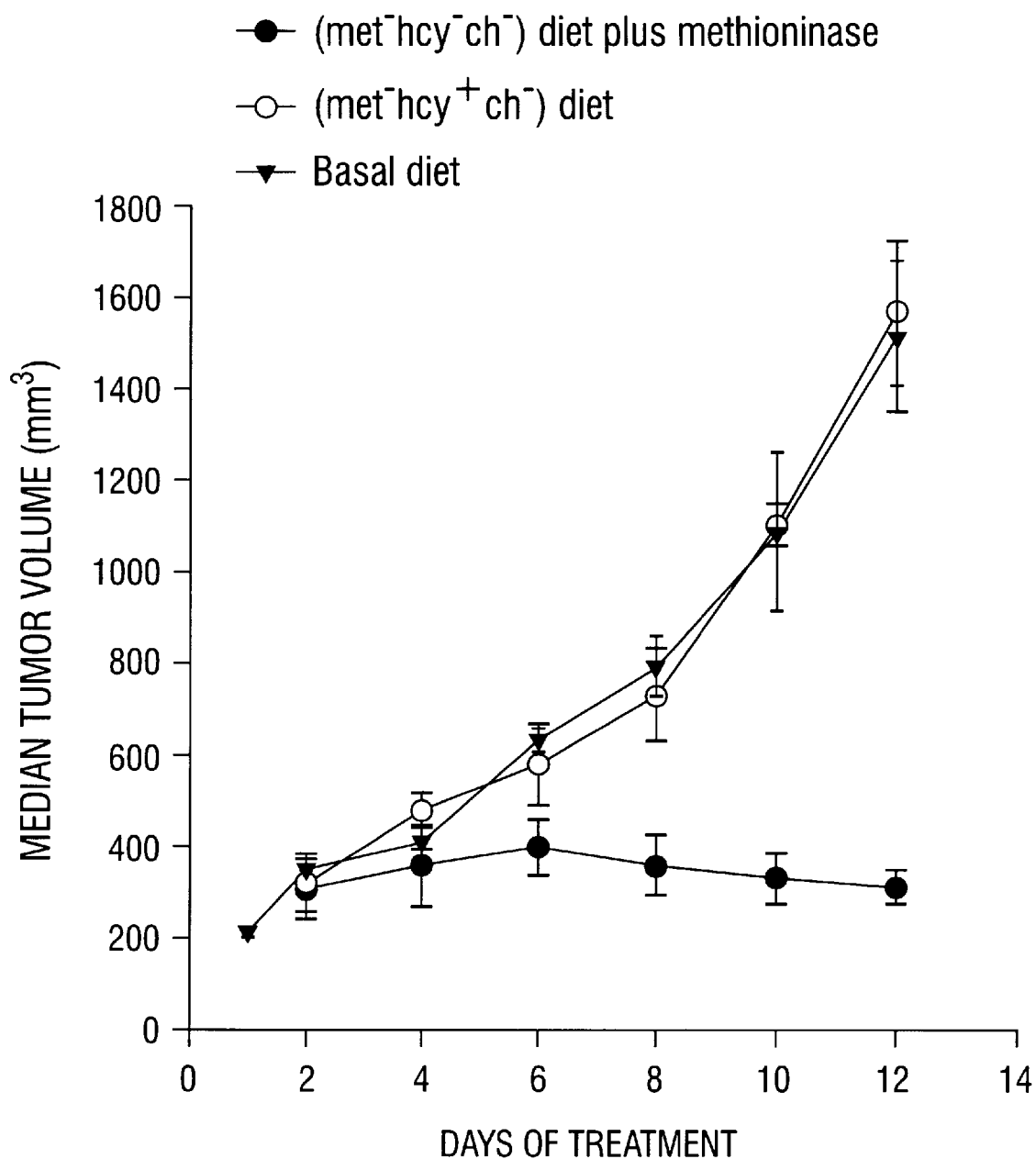
FIG. 9 shows the effect on median tumor volume during treatment with methioinnase/homocystine (filled circles) in tumor bearing athymic mice fed a met$^-$ch$^-$hcy$^-$ diet; the effect of met$^-$hcy$^+$chl$^-$ diet alone on (unfilled circles); and the effect of basal diet alone (filled triangles) on median tumor volume is also shown.
Figure 10:
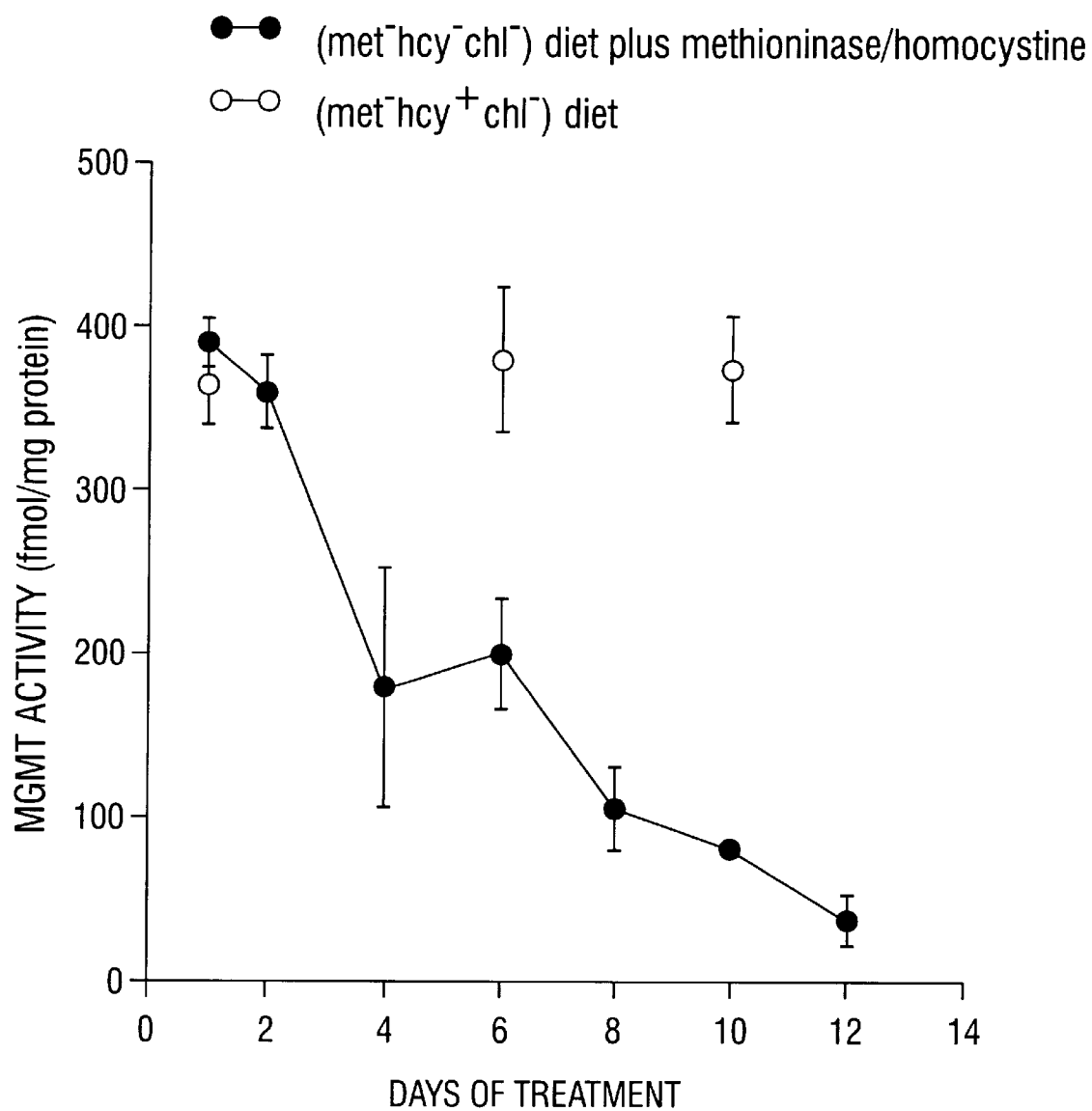
FIG. 10 shows the effect of a met$^-$ch$^-$hcy$^-$ diet combined with methioninase/homocystine (filled circles) on tumor MGMT activity during a 12 day regimen. No effect is observed in tumor MGMT in animals receiving a met$^-$hcy$^+$ chl$^-$ diet and non methioninase/homocystine treatment (open circles).

Daoy tumors were injected sc into thirty athymic mice fed a basal non-synthetic diet. When tumors grew to approximately 200 mm$^3$, one-third of the animals were transferred to a synthetic met$^+$hcy$^-$chl$^-$ diet (time 0), one-third to a synthetic met$^-$hcy$^-$chl$^-$ diet, while the rest were kept on the basal diet. Animals on the met$^-$hcy$^-$chl$^-$ diet were injected ip with homocystine (50 mg/kg daily) and with methioninase (1000 u/kg twice per day). Tumors grew rapidly in animals fed the basal diet as expected and also in animals fed the met$^-$hcy$^+$chl$^-$ diet. On the other hand, growth of tumors in animals deprived of dietary methionine and homocysteine were retarded after reaching a median volume of 400 mm$^3$ (FIG. 9). At the conclusion of this experiment, animals were killed and plasma methionine levels were determined. As shown in TABLE 6, treatment with methioninase/homocystine in combination with a met$^-$hcy$^-$chl$^-$ diet markedly reduced the levels of plasma methionine. Animals were killed during these treatments at the intervals shown in FIG. 10 (three animals per time point). Tumors were excised and MGMT activity was measured in non-necrotic parts of the tumor. Tumor MGMT activity declined from 400 fmol/mg protein to about 50 fmol/mg protein within 12 days from initiation of treatment with this methionine depleting regimens. In comparison, MGMT activity did not decline in normal tissue as shown in TABLE 7. MGMT activity did not fluctuate in tumors of animals fed the basal diet. Thus, the present invention has identified a regimen that depletes plasma methionine while allowing the animal to maintain a constant weight. This regimen does not deplete other sulfur amino acids or lower glutathione levels in the plasma. When tumor bearing animals were treated with this regimen, tumor growth was retarded. Most importantly, the MGMT activity in mer+ tumors was markedly reduced. This treatment destabilizes the tumor inducing extensive cell death (necrosis), inhibition of mitosis and loss of DNA repair functions. The latter is shown to sensitize the tumor to conventional chemotherapeutic alkylating drugs.

TABLE 6

Depletion of plasma methionine in tumor bearing athymic mice correlates with tumor stasis and regression

| Diet | Treatment | Tumor Volume | Plasma Methionine |
| --- | --- | --- | --- |
| basal (n = 6) | None | 1509 ± 164[a] | 36 ± 6 |
| met$^-$hcy$^+$chl$^-$ (n = 6) | None | 1564 ± 171 | 35 ± 12 |
| met$^-$hcy$^-$chl$^-$ (n = 6) | Methioninase/homocysteine | 379 ± 22c | 15 + 1c |
| met$^-$hcy$^-$chl$^-$ (n = 2) | Methioninase/homocysteine | 251, 237c | 7, 5c |

[a]Mean of three tumor ± sd.
[b]Animals in which tumors were static were separated from those in which tumor regression was observed.
c Six animals with tumors of approximately 200 mm3 were placed on a methionine, homocysteine, choline, restricted diet and treated with methioninase/homocysteine at 12 hours intervals for 12 days. Controls were kept on either basal or methionine, choline restricted diets. Animals in which tumor remained static (n = 4) were separated from those in which the tumor regressed (n = 2).

TABLE 7

Effect of diet and tumor burden on hepatic MGMT in athymic mice.

| Diet | Tumor | Liver MGMT |
| --- | --- | --- |
| basal | − | 110 ± 4 |
| basal | + | 109 ± 9 |
| synthetic (met-hcy+chl-)[1] | − | 181 ± 15 |
| synthetic (met-hcy+chl-)[1] | − | 189 ± 21 |
| synthetic (met-hcy+chl-)[2] | + | 95 ± 6 |

[1]Animals kept on diets for 15 days.
[2]Animals treated with methioninase and homocysteine for at least 12 days prior to MGMT measurements.

The following references were cited herein:

BRADFORD M. (1976). A rapid and sensitive method for the quantitation of microgram quantities of protein utilizing the principle of protein-dye binding. *Anal. Biochem.* 72, 248–254.

BRANCH et al., (1993). Defective mismatch binding and a mutator phenotype in cells tolerant to DNA damage. *Nature*, 362, 652–654.

BREILLOUT et al., (1990). Methionine dependency of malignant tumors: A possible approach for therapy. *J. Natl. Cancer Inst.*, 82, 1628–1632.

BREILLOUT et al., (1987). Decreased rat rhabdomyosarcoma pulmonary metastasis in response to a low methionine diet. *Anti Cancer Res.*, 7, 861–867.

BRENT et al., (1993). Identification of nitrosourea-resistant human rhabdomyosarcomas by in situ immunostaining of O$^6$-methylguanine-DNA methyltransferase. *Oncol. Res.*, 5, 83–86.

BRENT et al., (1991). In vivo stability of human O$^6$-methylguanine-DNA methyltransferase. *Am. Assoc. Cancer Res.*, 32, 2505.

COSTELLO et al., (1994). Methylation-related chromatin structure is associated with exclusion of transcription factors from and suppressed expression of the O$^6$-methylguanine DNA methyltransferase gene in human glioma cell lines. *Mol. Cell Biol.*, 14, 6515–6521.

DAY et al., (1980). Defective repair of alkylated DNA by human tumor and SV40 transformed human cell strains. *Nature*, 288, 724–727.

DOLAN et al., (1990). Modulation of mammalian O$^6$-alkylguanine-DNA alkyltransferase in vivo by O$^6$-benzylguanine and its effects of the sensitivity of a human glioma tumor to 1-(2-chloroethyl)-3-(4-methylcyclohexyl)-1-nitrosourea. *Cancer Commun*, 2, 371–377.

DOLAN et al., (1993). Effect of O$^6$-benzylguanine on the sensitivity of human colon tumor xenografts to 1,3-bis (2-chloroethyl)-1-nitrosourea (BCNU). *Biochem. Pharm.*, 46, 285–290.

DUNN et al., (1986). Cell cycle dependent modulation of O$^6$-methylguanine-DNA-methyltransferase in C3H/10T1/2 cells. *Carcinogenesis*, 7, 807–812.

DUNN et al., (1991). The role of O$^6$-alkylguanine in cell killing and mutagenesis in Chinese hamster ovary cells. *Carcinogenesis*, 12, 8389.

EGYHAZI et al., (1991). Carmustine-induced toxicity, DNA crosslinking and O$^6$-methylguanine-DNA methyltransferase activity in two human lung cancer cell lines. *Eur. J. Cancer*, 27, 1658–1662.

FINKELSTEIN J D. (1990). Methionine metabolism in mammals. *J. Nutr. Biochem.*, 1, 228–237.

FISKERSTRAND, et al., (1994). Development and reversion of methionine dependence in a human glioma cell line: relation to homocysteine remethylation and cobalamin status. *Cancer Res.* 54, 4899–4906.

GERSON et al., (1985). O⁶-alkylguanine-DNA alkyltransferase activity in human myeloid cells. *J. Clin. Invest.*, 76, 2106–2114.

GOSEKI et al., (1992). Antitumor effect of methionine-depleting total parenteral nutrition with doxorubicin administration on Yoshida sarcoma-bearing rats. *Cancer,* 69, 1865–1872.

GUO et al., (1993a). Expression of the biochemical defect of methionine dependence in fresh patient tumors in primary histoculture. *Cancer Res.*, 53, 2479–2483.

GUO et al., (1993b). Therapeutic tumor-specific cell cycle block induced by methionine starvation in vivo. Cancer Res., 53, 5676–5679.

HALPERN et al., (1974). The effect of replacement of methionine by homocysteine on survival of malignant and normal adult mammalian cells in culture. *Proc. Natl. Acad. Sci. USA,* 71, 1133–1136.

HARRIS et al., (1991). Characterization of the promoter region of the human O⁶-methylguanine-DNA methyltransferase gene. *Nucleic Acids Res.* 19, 6163–6167.

HARRIS et al., (1994). In vitro methylation of the human O⁶-methylguanine-DNA methyltransferase promoter reduces transcription. *Biochi. Biophys. Acta,* 1217, 141–146.

HOFFMAN R M. (1990). Unbalanced transmethylation and the perturbation of the differentiated state leading to cancer. *BioEssays,* 12, 163–166.

HOFFMAN R M AND ERBE R W. (1976). High in vivo rates of methionine biosynthesis in transformed human and malignant rat cells auxotrophic to methionine. *Proc. Natl. Acad. Sci. USA,* 73, 1523–1527.

HORI et al., (1996). Gene cloning and characterization of *Pseudomonas putida* L-methionine-alpha-deamino-gamma-mercaptomethane-lyase. Cancer Res., 56, 2116–2122.

HOSHIYA et al., (1995). Human tumors are methionine dependent in vivo. *Anticancer Res.,* 15, 717–718.

JACKSON R C. (1992). Cell cycle effects of drugs. In: *The Theoretical Foundations of Cancer Chemotherapy Introduced by Computer Models.* R. C. Jackson (ed.) Academic Press Inc.:San Diego.

JOHNSON B A, ASWAD D W. (1993). Kinetic properties of bovine brain protein L-isoaspartyl methyltransferase determined using a synthetic isoaspartyl peptide substrate. *Neurochem. Res.,* 18, 87–94.

JUDDE et al., (1989). Biochemical analysis of the role of transmethylation in the methionine dependence state. *Cancer Res.,* 49, 4859–4865.

KOKKINAKIS et al., (1996). Mechanism of depletion of O⁶-Methylguanine-DNA methyltransferase activity in rat tissues by O⁶-Benzyl-2'-deoxyguanosine. Role of metabolism. *Anticancer Res.,* 16, 1–10.

KROES et al., (1995). The role of mRNA stability and transcription on O6-methylguanine-DNA methyltransferase (MGMT) expression in Mer− human tumor cells. *Carcinogenesis,* 16, 2255–2257.

KUBOTA et al., (1995). Methionine uptake by tumor tissue: a microautoradiographic comparison with FDG. *J. Nucl. Med.,* 36, 484–492.

LAEMMLI U K. (1970). Cleavage of structural proteins during assembly of the head of bacteriophage T4. *Nature,* 27, 680–685.

LISHKO et al., (1993). Depletion of serum methionine by methioninase in mice. *Anticancer Res.,* 13, 1465–1468.

LITEPLO R G. (1990). Reversion to a homocysteine-responsive phenotype in a human melanoma cell line is associated with diminished growth potential and increased methionine biosynthesis. *Exp. Cell Res.,* 186, 340–345.

LITEPLO et al., (1991). Changes in cobalamin metabolism are associated with the altered methionine auxotrophy of highly growth autonomous human melanoma cells. *J. Cell Physiol.,* 149, 332–338.

MARATHI et al., (1993). Prolonged depletion of O⁶-methylguanine DNA methyltransferase activity following exposure to O⁶-benzylguanine with or without streptozotocin enhances 1,3-bis(2-chloroethyl)-1-nitrosourea sensitivity in vitro. *Cancer Res.,* 53, 4281–4286.

MATSUDAIRA P. (1987). Sequence from picomole quantities of proteins electroblotted onto polyvinylidene difluride membranes. *J. Biol. Chem.,* 262, 10035–10038.

MINEURA et al., (1993). (14C-Methyl)-L-methionine uptake in rat brain tumors before and after treatment with the protein synthesis inhibitor cycloheximide. *J. Neuro-Oncol.,* 15, 229–233.

PEGG A E. (1984). S-adenosylmethionine decarboxylase: a brief review. *Cell Biochem. Funct.,* 2, 11–15.

PIEPER et al., (1991). Direct correlation between methylation status and expression of the human O⁶-methylguanine DNA methyltransferase gene. *Cancer Comm.,* 3, 241–253.

QIAN et al., (1995). Localization of methylation sites in the human O⁶-methylguanine-DNA methyltransferase promoter: correlation with gene suppression. *Carcinogenesis.* 16, 1385–90.

SAMBROOK et al., (1989). *Molecular Cloning: A Laboratory Manual.* 2nd Ed. Cold Spring Harbor Laboratory Press:Cold Spring Harbor.

SCHOLD et al., (1989). O⁶-alkylguanine-DNA alkyltransferase and sensitivity to procarbazine in human tumor xenografts. *J. Neurosurg.* 70, 573–577.

SCHOLD et al., (1996). Treatment of human brain tumor xenografts with O⁶-benzyl-2'-deoxyguanosine and BCNU. *Cancer Res.,* 56, 2076–2081.

STERN P H, HOFFMAN R M (1984). Elevated rates of transmethylation in cell lines from diverse human tumors. In Vitro *Rapid Commun. Cell Biol.,* 20, 663–670.

STERN P H, HOFFMAN R M (1986). Enhanced in vitro selective toxicity of chemotherapeutic agents for human cancer cells based on a metabolic defect. *J. Natl. Cancer Inst.,* 76, 629–639.

TANO et al., (1990) Isolation and structural characterization of a cDNA clone encoding the human repair protein for O⁶-alkylguanine. *Proc. Natl. Acad. Sci. USA,* 87, 686–690.

TAUTT et al., (1982). Methionine regulation of N-5-Methyltetrahydrofolate: homocysteine methyltransferase and its influence on the growth and protein synthesis in normal, neoplastic, and transformed cells in culture. *J. Natl. Cancer Inst.,* 69, 9–14.

TSUJIMURA et al., (1987). O⁶-methylguanine methyltransferase activity and sensitivity of Japanese tumor cell strains to 1-(4-amino-2-methyl-5-pyrimidinyl)methyl-3-(2-chloroethyl)-3-nitrosourea hydrochloride. *Jap. Cancer Res.,* 78, 1207–1215.

VANHAMME L, SZPIRER C. (1989). Spontaneous and 5-azacytidine-induced revertants of methionine-dependent tumor-derived and H-ras-1-transformed cells. *Exp. Cell Res.,* 181, 159–168.

VON WRONSKI M, BRENT T. (1994). Effect of 5-azacytidine on expression of the human DNA repair enzyme O⁶-methylguanine-DNA methyltransferase. *Carcinogenesis,* 15, 577–582.

VON WRONSKI et al., (1992). Cytosine methylation and suppression of O⁶-methylguanine-DNA methyltransferase expression in human rhabdomyosarcoma cell lines and xenografts. *Oncol. Res.,* 4, 167–174.

WANG et al., (1992) Correlation between DNA methylation and expression of $O^6$-methylguanine-DNA methyltransferase gene in cultured human tumor cells. *Mutation Res.,* 273, 221–230.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of depleting methionine in the plasma of an individual in need of such treatment, comprising the steps of:

restricting intake of methionine, homocysteine and choline in the diet of said individual;

administering to said individual a pharmacologically effective amount of a methionine scavenger; and treating said individual with an effective amount of homocystine.

2. The method of claim 1, wherein said methionine scavenger is 1-methionine-α-deamino-γ-mercaptomethane-lyase.

3. The method of claim 2, wherein said 1-methionine-α-deamino-γ-mercaptomethane-lyase is administered intravenously in an amount of about 200 u/kg.

4. The method of claim 2, wherein said 1-methionine-α-dea-γ-mercaptomethane-lyase is administered intraperitoneally in an amount of about 1000 u/kg.

5. The method of claim 1, wherein said homocystine is administered in an amount of from about 20 mg/kg to about 50 mg/kg.

6. The method of claim 5, wherein said homocystine is administered in twice daily, about 2 hours after the methionine scavenger for a period of 10–12 days.

7. The method of claim 1, wherein the plasma concentration of methionine after the administration of the methionine scavenger and homocystine is from about 1 $\mu$M to about 7 $\mu$M.

8. The method of claim 1, wherein the concentration of cysteine, glutathione, total homocysteine, and essential amino acids other than methionine is not adversely affected.

* * * * *

UNITED STATES PATENT AND TRADEMARK OFFICE
CERTIFICATE OF CORRECTION

PATENT NO. : 6,017,962

DATED : January 25, 2000

INVENTOR(S) : Clifford S. Schold and Demetrius M. Kokkinakis

It is certified that error appears in the above-identified patent and that said Letters Patent is hereby corrected as shown below:

In the Abstract, line 6, please delete "of method".

In claim 4, column 22, line 2, please delete "dea" and insert therefor -- deamino --.

Signed and Sealed this

Twenty-eighth Day of November, 2000

Attest:

Q. TODD DICKINSON

*Attesting Officer*  *Director of Patents and Trademarks*